US008227252B2

(12) United States Patent
Lawry et al.

(10) Patent No.: US 8,227,252 B2
(45) Date of Patent: Jul. 24, 2012

(54) MULTIPLEX ANALYSIS OF STACKED TRANSGENIC PROTEIN

(75) Inventors: John R. Lawry, Westfield, IN (US); Joshua A. Flook, Tipton, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 12/793,058

(22) Filed: Jun. 3, 2010

(65) Prior Publication Data

US 2010/0313290 A1 Dec. 9, 2010

Related U.S. Application Data

(60) Provisional application No. 61/183,777, filed on Jun. 3, 2009.

(51) Int. Cl.
*A01H 1/04* (2006.01)
*A01H 1/00* (2006.01)
*C40B 30/10* (2006.01)
*C40B 30/00* (2006.01)

(52) U.S. Cl. ............ 436/86; 800/295; 800/260; 506/12; 506/7

(58) Field of Classification Search .................... 436/86; 800/260, 295; 506/12, 7
See application file for complete search history.

(56) References Cited

U.S. PATENT DOCUMENTS

2005/0153380 A1 7/2005 Everett et al.
2005/0229273 A1 10/2005 Huang et al.

OTHER PUBLICATIONS

PCT International Search Report for International Application No. PCT/US2010/037192, mailed Sep. 7, 2010.
PCT Written Opinion for International Application No. PCT/US2010/037192, mailed Sep. 7, 2010.
Sesikeran and Vasanthi, "Constantly evolving safety assessment protocols for GM Foods," Asia Pac .J. Clin. Nutr. 17 Supple. 1:241-244, (2008).
Alwine et al. "Method for detection of specific RNAs in agarose gels by transfer to diazobenzyloxymethyl-paper and hybridization with DNA probes," Proc. Nat. Acad. Sci. 74:5350-5354 (1977).
Chang et al, "Patterns of protein synthesis and tolerance of anoxia in root tips of maize seedlings acclimated to a low-oxygen environment, and identification of proteins by mass spectrometry," Plant Physiology, vol. 122, pp. 295-317 (2000).
Baldwin, "Protein Identification by Mass Spectrometry," Mol. Cel. Proteomics, (1):1-9, (2004).

*Primary Examiner* — Christine T Mui
(74) *Attorney, Agent, or Firm* — Eric J. Kraus; TraskBritt, P.C.

(57) ABSTRACT

The invention relates to methods for multiplex analysis of complex protein samples from plants using mass spectroscopy. In some embodiments, the disclosure concerns methods for maintaining a transgenic plant variety, for example by analyzing generations of a transgenic plant variety for presence and concentration of multiplexed transgenic proteins.

17 Claims, 30 Drawing Sheets

Cry1F (Pesticidal crystal protein cry1Fa (Insecticidal delta-endotoxin Cry1F(a)))
T22 TYPIQTSSQLTR (SEQ ID NO:7)
T46 IFAGQFNK (SEQ ID NO:8)

Cry35 (Cry35Ab-like [Bacillus thuringiensis])

T9 VLTAGTGQALGLIR (SEQ ID NO:10)

T17 YQYWQR (SEQ ID NO:11)

PAT (Phosphinothricin N-acetyltransferase (PPT N-acetyltransferase))

T2 TEPQTPQEWIDDLER (SEQ ID NO:12)

T8 LGLGSTLYTHLLK (SEQ ID NO:13)

T10 SVVAVIGLPNDPSVR (SEQ ID NO:14)

Cry34 (crystal protein ET79 [Bacillus thuringiensis])

T7 TSPTNVAN

MULTIPLEX ANALYSIS OF STACKED TRANSGENIC PROTEIN

This application claims a priority based on provisional application 61/183,777 which was filed in the U.S. Patent and Trademark Office on Jun. 3, 2009, the entire disclosure of which is hereby incorporated by reference.

TECHNICAL FIELD

The invention generally relates to high-throughput analysis of plant traits. In certain embodiments, the invention relates to methods of high-throughput analysis and quantitation of plant proteins determined by mass spectrometry with a single injection of complex protein samples derived from plants and plant tissue. Certain embodiments further relate to methods of analyzing genotypes of transgenic plants and maintaining the expression in those plants of desirable plant traits.

BACKGROUND

The increasing use of recombinant DNA technology to produce transgenic plants for commercial and industrial use requires the development of high-throughput methods of analyzing transgenic plant lines. Such methods are needed to maintain transgenic plant varieties through successive generations, to prevent the escape of transgenes into the environment, and to assist in the rapid development of transgenic plants with desirable or optimal phenotypes. Moreover, current guidelines for the safety assessment of GM plants proposed for human consumption requires characterization at the DNA and protein level between the parent and transformed crop. Sesikeran and Vasanthi (2008) *Asia Pac. J. Clin. Nutr.* 17 Suppl. 1:241-44. New plant varieties that are developed consist of increasingly complex genetic modifications including, inter alia, stacked genes and traits.

The current methods for analysis of transgenic plants that are preferred in the art are: DNA-based techniques (e.g. PCR); RT-PCR; the use of reporter genes; Southern blotting; and immunochemistry. All of these methodologies suffer from various shortcomings, and a superior method that is broadly able to rapidly and inexpensively identify and quantitate multiple transgenic gene products in a high-throughput manner from a limited sample from a transgenic plant is desired.

DNA-based techniques for transgenic plant analysis suffer from several notable deficiencies. Despite the fact that *Agrobacterium*-mediated transformation is the most preferred method of genetic plant transformation, the genotypes of *Agrobacterium*-transformed plants are difficult to analyze by PCR-based methodologies. See Nain et al. (2005) *Plant Mol. Biol. Rep.* 23:59-65. The presence of even trace amounts of *Agrobacterium* in transformed tissues yields misleading PCR results. Id. DNA amplification formats also require empirical testing of gene-specific primers and thermocycler conditions. Most significantly, DNA-based approaches for screening transgenic plants do not actually determine expression of the gene product protein. Similarly, RT-PCR or Northern blot analysis may be used to confirm the presence of transgene transcripts in transgenic plant material. Alwine et al. (1977) *Proc. Nat. Acad. Sci.* 74:5350-54; Toplak et al. (2004) *Plant Mol. Biol. Rep.* 22:237-50. Neither do these methods confirm the presence of actual protein expression in the source plant material. These techniques also require the use of radioactive materials and/or large amounts of tissue and processing time.

Reporter genes, such as genes encoding fluorescent proteins, may also be co-transformed into transgenic plants to provide a tool to identify transformants. However, reporter genes are only indirect reporters of genetic recombination. Expression of the reporter gene construct does not confirm expression of the accompanying transgene. Further, either the reporter gene or the transgene may be lost in successive generations of the host plant, thereby uncoupling presence of the reporter from the transgene of interest. Similarly, transgenes may escape from the host plant into neighboring plants, for example by cross-pollination, without concurrent escape of the reporter gene. When multiple genes are stacked in a transgenic plant, an equal number of reporter genes would have to be introduced to analyze the transgenic proteome, and since reporter gene function is only an indirect reporter of transgene function, changes in expression of one transgene in response to the presence of an additional transgene would not be detected.

Unlike the methods outlined above, immunochemistry can be used to identify products of transgene expression in a transgenic plant. Though immunochemistry is useful for this purpose, the method requires highly-purified protein samples for antibody production. The resulting antibodies must be tested for specificity, and reagent-specific assay conditions must be developed. The high levels of expression and purification required to conduct immunochemistry, as well as the related problem of removing contaminants from the plant tissue, are limitations on the utility of this method.

Mass spectrometry may also be used to analyze the proteome of a transgenic plant. However, art-recognized spectrometric techniques require complex mixtures of plant proteins to be first separated by 2-D gel electrophoresis. Rajagopal and Ahern (2001) *Science* 294(5551):2571-73; See also Domon and Aebersold (2006) *Science* 312(5771): 212-17, 214. Single bands from the gel-separated protein sample may then be digested with a protease and subjected to mass spectrometry to identify the unique protein originally present in the undigested band. See, e.g., Chang et al. (2000) *Plant Physiol.* 122(2):295-317. The gel-separation step in this method is a time-consuming process that impedes the use of mass spectrometry in high-throughput applications.

There is a need in the art for a high-throughput method for detecting and quantitating the presence of products of transgene expression in plants that does not require purified or highly-expressed protein, or method-specific reagents. This method will be useful in helping cultivators and growers of transgenic plants maintain the phenotype of the target transgenic plant variety through successive generations of sexual and/or asexual reproduction. The method will also be useful in rapidly analyzing product plants of a transformation procedure to identify those product plants that are transgenic plants and express the introduced protein in desired tissues. Further, the method may be used to rapidly screen plants at risk of being contaminated with transgenes from a transgenic plant, in order to accomplish bioconfinement of the transgenic plant.

SUMMARY OF THE DISCLOSURE

A particular embodiment of the invention includes a high-throughput method of detecting and quantitating the presence of two or more proteins of interest with known amino acid sequences in a plant-based sample. The method includes providing a first injection of a complex plant-based sample comprising proteins and digesting the complex plant-based sample proteins into peptides. Alternately, the method includes a preliminary step of digesting the complex plant-based sample proteins into peptides followed by providing a first injection of the peptides. The peptides are then separated and ionized. Simultaneous mass spectral data are obtained for the peptides and the presence or absence of the two or more proteins of interest is determined.

Another embodiment of the invention includes a high-throughput method of detecting the presence of two or more proteins of interest with known amino acid sequences in a plant-based sample. The method includes providing mass spectral data for two or more proteins of interest and providing a first injection of a complex plant-based sample comprising proteins. The complex plant-based sample proteins are digested into peptides and the peptides are then separated and ionized. Simultaneous mass spectral data are obtained for the peptides. The simultaneous mass spectral data are compared to the mass spectral data provided for the two or more proteins of interest, thereby determining the presence or absence of the two or more proteins of interest.

Yet another embodiment of the invention includes a method of maintaining the genotype of a transgenic plant variety. The method includes: (i) providing mass spectral data for one or more expected product(s) of transgene expression in the transgenic plant variety; (ii) providing a first injection of a complex sample comprising proteins from a first generation of the transgenic plant variety; (iii) digesting the complex plant-based sample proteins into peptides; (iv) separating the peptides; (v) ionizing the peptides; (vi) obtaining simultaneous mass spectral data for the peptides, and comparing the simultaneous mass spectral data to the mass spectral data provided for the expected products of transgene expression, thereby determining the presence or absence of the expected products of transgene expression in the first generation of the transgenic plant variety; (vii) providing a first injection of a complex sample comprising proteins from a second generation of the transgenic plant variety; (viii) repeating steps (iii)-(vi) with the complex sample comprising proteins from the second generation of the transgenic plant variety; and (ix) failing to propagate the second generation of the transgenic plant variety if the presence of the expected product(s) of transgene expression cannot be confirmed in the mass spectral data for the peptides from the complex protein sample from the second generation of the transgenic plant variety, thereby maintaining the genotype of the transgenic plant variety.

BRIEF DESCRIPTION OF THE FIGURES

FIG. 1 shows LC/MS/MS multiplex detection of AAD-1.

FIG. 2 shows LC/MS/MS multiplex detection of AAD-12.

FIG. 3 shows LC/MS/MS multiplex detection of Cry1F.

FIG. 4 shows LC/MS/MS multiplex detection of Cry34.

FIG. 5 shows LC/MS/MS multiplex detection of Cry35.

FIG. 6 shows LC/MS/MS multiplex detection of PAT.

FIG. 7 shows LC/MS/MS multiplex detection of Cry1F, expressed in inbred maize tissue.

FIG. 8 shows LC/MS/MS multiplex detection of Cry34, expressed in inbred maize tissue.

FIG. 9 shows LC/MS/MS multiplex detection of Cry35, expressed in inbred maize tissue.

FIG. 10 shows LC/MS/MS multiplex detection of PAT, expressed in inbred maize tissue.

DETAILED DESCRIPTION

Figure 1A:
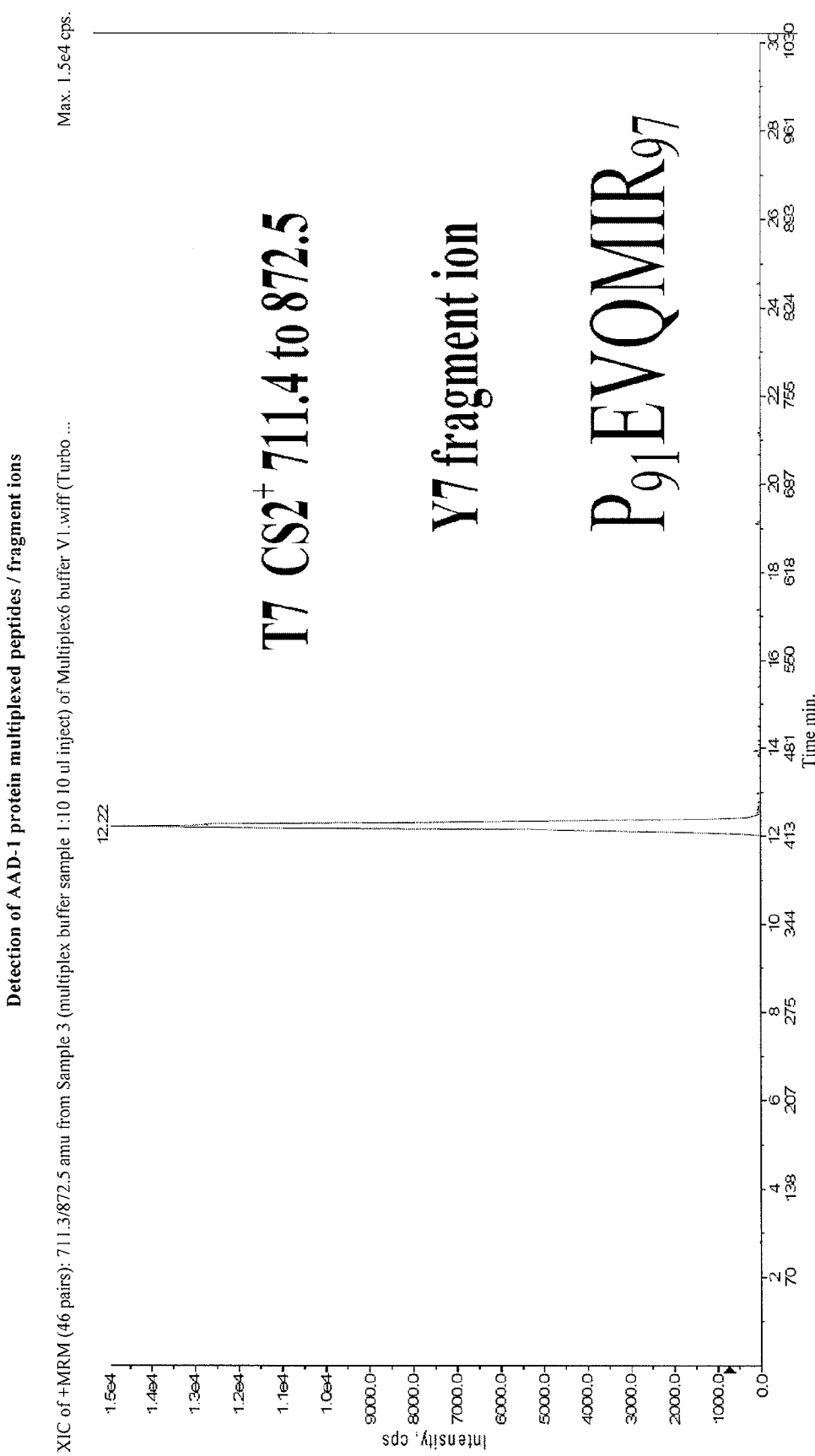
FIG. 1a includes detection of T7 peptide Y7 fragment ion PEVQMIR (SEQ ID NO:15).

The specificity allowed in a mass spectrometry approach for identifying a single protein from a complex sample is unique in that only the sequence of the protein of interest is required in order to identify the protein of interest. Compared to other formats of multiplexing, mass spectrometry is unique in being able to exploit the full length of a protein's primary amino acid sequence to target unique identifier-type portions of a protein's primary amino acid sequence to virtually eliminate non-specific detection. In some embodiments of the present invention, a proteolytic fragment or set of proteolytic fragments that uniquely identifies a protein(s) of interest is used to detect the protein(s) of interest in a complex protein sample.

In broad terms, particular methods of the invention allow for any protein(s) to be monitored directly and quantitated from the tissue of interest requiring only prior knowledge of the protein(s) amino acid sequence. The method can be performed in a high-throughput manner without the need to develop/test a method-specific detection reagent. Having purified protein as a reagent for method development is always beneficial, but for this analysis a protein that can only be purified to, for example, 60% can still be adequate for method development. Methods according to the present disclosure can eliminate the need for one of skill in the art to develop often challenging methods to prepare highly-purified protein samples to use for antibody production. Therefore, methods of the present disclosure can save time and resources. Moreover, the methods provide more variety of protein reagents suitable for multiplex analysis, since the efforts to remove, for example, the final 30-40% of contaminants, may not be required. Disclosed methods also represent a needed improvement over DNA amplification-based multiplex approaches, which require empirical testing of gene specific primers and thermocycler conditions, and which moreover create situations where any lack of target specificity can significantly decrease method accuracy due to the exponential amplification required for DNA detection.

In particular embodiments, methods of the present invention enable protein reverse engineering to determine why a particular protein has its unique properties without requiring the actual protein to begin a study. For example, sequence modifications and/or post-translational modifications of target proteins that are associated with desirable or undesirable plant traits may be identified from mass spectral data from a complex protein sample from a plant expressing the desirable or undesirable trait.

In some embodiments, disclosed methods enable the quantification or determination of ratios of multiple proteins in a complex protein sample by a single mass spectrometry analysis, as opposed to measuring each protein of interest individually multiple times and compiling the individual results into one sample result.

In yet other embodiments, the present disclosure also provides methods useful for the development and use of transgenic plant technology. Specifically, disclosed methods may be used to maintain the genotype of transgenic plants through successive generations. Also, some embodiments of the methods disclosed herein may be used to provide high-throughput analysis of non-transgenic plants that are at risk of being contaminated with transgenes from neighboring plants, for example, by cross-pollination. By these embodiments, bioconfinement of transgenes may be facilitated and/or accomplished. In other embodiments, methods disclosed herein may be used to screen the results of a plant transformation procedure in a high-throughput manner to identify transformants that exhibit desirable expression characteristics.

I. Abbreviations

The present invention will be described with reference to the following abbreviations:

AAD-1 (R)-2,4-dichlorophenoxypropionate dioxygenase
AAD-12 (S)-2,4-dichlorophenoxypropionate/alpha-ketoglutarate dioxygenase
CID Collision-induced dissociation
Cry 1F Pesticidal crystal protein cry 1Fa (Insecticidal delta-endotoxin Cry1F(a))
Cry34 crystal protein ET79 (*Bacillus thuringiensis*)
Cry35 Cry35Ab-like (*Bacillus thuringiensis*)
CE capillary eletrophoresis
DNA deoxyribonucleic acid
ELISA enzyme-linked immunosorbent assay
EPI enhanced product ion
GM genetically modified
IDA information-dependent acquisition
LC\MS\MS liquid chromatography-tandem mass spectrometry
MRM multiple reaction monitoring
MS mass spectrometry
MSMS tandem mass spectrometry
PAT Phosphinothricin N-acetyltransferase (PPT N-acetyltransferase)
PCR polymerase chain reaction
RT-PCR reverse transcription polymerase chain reaction II. Terms In order to facilitate review of the various embodiments of the disclosure, the following explanation of specific terms are provided:

Bioconfinement: As used herein, the term "bioconfinement" refers to restriction of the movement of genetically modified plants or their genetic material to designated areas. The term includes physical, physicochemical, biological confinement, as well as other forms of confinement that prevent the survival, spread or reproduction of a genetically modified plants in the natural environment or in artificial growth conditions.

Complex protein sample: As used herein, the term "complex protein sample" is used to distinguish a sample from a purified protein sample. A complex protein sample contains multiple proteins, and may additionally contain other contaminants.

Mass spectrometry: As used herein, the general term "mass spectrometry" refers to any suitable mass spectrometry method, device or configuration including, e.g., electrospray ionization (ESI), matrix-assisted laser desorption/ionization (MALDI) MS, MALDI-time of flight (TOF) MS, atmospheric pressure (AP) MALDI MS, vacuum MALDI MS, tandem MS, or any combination thereof. Mass spectrometry devices measure the molecular mass of a molecule (as a function of the molecule's mass-to-charge ratio) by measuring the molecule's flight path through a set of magnetic and electric fields. The mass-to-charge ratio is a physical quantity that is widely used in the electrodynamics of charged particles. The mass-to-charge ratio of a particular peptide can be calculated, a priori, by one of skill in the art. Two particles with different mass-to-charge ratio will not move in the same path in a vacuum when subjected to the same electric and magnetic fields. The present invention includes, inter alia, the use of high performance liquid chromatography (HPLC) followed by tandem MS analysis of the peptides.

Mass spectrometry instruments consist of three modules: an ion source, which splits the sample molecules into ions; a mass analyzer, which sorts the ions by their masses by applying electromagnetic fields; and a detector, which measures the value of an indicator quantity and thus provides data for calculating the abundances of each ion present. The technique has both qualitative and quantitative applications. These include identifying unknown compounds, determining the isotopic composition of elements in a molecule, determining the structure of a compound by observing its fragmentation, and quantifying the amount of a compound in a sample.

A detailed overview of mass spectrometry methodologies and devices can be found in the following references which are hereby incorporated by reference: Can and Annan (1997) Overview of peptide and protein analysis by mass spectrometry. In: *Current Protocols in Molecular Biology*, edited by Ausubel, et al. New York: Wiley, p. 10.21.1-10.21.27; Paterson and Aebersold (1995) *Electrophoresis* 16: 1791-1814; Patterson (1998) Protein identification and characterization by mass spectrometry. In: *Current Protocols in Molecular Biology*, edited by Ausubel, et al. New York: Wiley, p. 10.22.1-10.22.24; and Domon and Aebersold (2006) *Science* 312(5771):212-17.

Multiplex: As the term is used herein, proteins and/or peptides are "multiplexed" when two or more proteins and/or peptides of interest are present in the same sample.

Plant trait: As used herein, a "plant trait" may refer to any single feature or quantifiable measurement of a plant.

Peptide: Peptides are short polymers formed from the linking, in a defined order, of α-amino acids. Peptides may also be generated by the digestion of polypeptides, for example proteins, with a protease.

Protein: Proteins are organic compounds made of amino acids arranged in a linear chain and joined together by peptide bonds between the carboxyl and amino groups of adjacent amino acid residues. The sequence of amino acids in a protein is defined by the sequence of a gene, which is encoded in the genetic code. In general, the genetic code specifies 20 standard amino acids, however in certain organisms the genetic code can include selenocysteine—and in certain archaea-pyrrolysine. The residues in a protein are often observed to be chemically modified by post-translational modification, which can happen either before the protein is used in the cell, or as part of control mechanisms. Protein residues may also be modified by design, according to techniques familiar to those of skill in the art. As used herein, the term "protein" encompasses linear chains comprising naturally occurring amino acids, synthetic amino acids, modified amino acids, or combinations of any or all of the above.

Single injection: As used herein, the term "single injection" refers to the initial step in the operation of a MS or LC-MS device. When a protein sample is introduced into the device in a single injection, the entire sample is introduced in a single step.

Stacked/stacking: As used herein, the term "stacked" refers to the presence of multiple heterologous polynucleotides incorporated in the genome of a plant.

Tandem mass spectrometry: In tandem mass spectrometry, a parent ion generated from a molecule of interest may be filtered in an MS instrument, and the parent ion subsequently fragmented to yield one or more daughter ions that are then analyzed (detected and/or quantified) in a second MS procedure.

Transgenic plant: As used herein, the term "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenic plants initially so altered as well as those created by sexual crosses or asexual propagation from the initial transgenic plant.

III. Selection Of Transgenic Protein For Multiplex Analysis

Any protein introduced into a plant via transgenic expression technology may be analyzed using methods of the invention. Proteins suitable for multiplex analysis according to the invention may confer an output trait that renders the transgenic plant superior to its nontransgenic counterpart. Non-limiting examples of desirable traits that may be conferred include herbicide resistance, resistance to environmental stress, enhanced yield, improved nutritional value, improved shelf life, altered oil content, altered oil composition, altered sugar content, altered starch content, production of plant-based pharmaceuticals, production of industrial products (e.g. polyhydroxyalkanoates: macromolecule polyesters considered ideal for replacing petroleum-derived plastics) and potential for bioremediation. Moreover, the expression of one or more transgenic proteins within a single plant species may be analyzed using methods of the present disclosure. The addition or modulation of two or more genes or desired traits into a single species of interest is known as gene stacking. Furthermore, the expression of one or more transgenic proteins may be analyzed concurrently in the presently disclosed multiplex analyses with one or more endogenous plant proteins.

Preference for the particular proteins to be analyzed is at the discretion of the artisan. Such proteins may be, but are not limited to, those from plants, animals, yeast, and the like and may be proteins either not found in a non-transformed cell or found in a transformed cell. Particularly suitable proteins that are expressed in transgenic plants are those that confer tolerance to herbicides, insects, or viruses, and genes that provide improved nutritional value, increased yields, drought tolerance, nitrogen utilization, production of useful industrial compounds, processing characteristics of the plant, or potential for bioremediation. Examples of useful proteins include the insecticidal gene from *Bacillus thuringiensis* for conferring insect resistance, and the 5'-enolpyruvyl-3'-phosphoshikimate synthase (EPSPS) gene and any variant thereof for conferring tolerance to glyphosate herbicides. As is readily understood by those skilled in the art, any protein conferring a desired trait may be expressed in a plant cell using recombinant DNA technology.

IV. Selection Of Peptide Fragments

Target proteins may be identified according to the present disclosure by determining the presence of proteolytic peptide fragments of the target proteins in MS spectra from a complex mixture of plant proteins. Protease enzymes cleave proteins at specific amino acid sequences that may be readily ascertained within the entire sequence of a target protein. Therefore, the set of peptide fragments to be produced by a digestion with one or more proteases can be deduced, a priori. A particular deduced peptide's unique mass to charge ratio may then be determined by its primary amino acid sequence.

Peptide fragments may also be ascertained empirically from MS spectra of digested target proteins. A particular embodiment of the invention could be selection of a peptide whose sequence is internal of predicted proteolytic cleavage sites. For empirical selection of peptide fragments for target protein identification, digested protein samples may be subjected to mass spectrometry to determine peptide fragments that provide the requisite detection sensitivity and specificity for multiplex protein identification. Generally, the most abundant ionized peptides are preferred for selection. The abundance of a particular ionized peptide is a function of the peptide abundance and the peptide's ionization efficiency.

The proteins of interest in a stacked product will be expressed at different levels relative to each other. The peptides detected will derive from the individual proteins being expressed in varying and sometime unknown concentrations. Detection of peptides and proteins will range from the atto-molar to micromolar concentrations. The purity of samples to be tested will range from purified standard proteins in buffer solutions, to crude plant matrix extracted from various tissues of interest. The peptide fragments will be identified in crude plant matrix as well as partially purified tissue sample matrix if target detection requires reducing the complexity of the sample matrix prior to detection.

V. Targeted Mrm Analysis

Once one or more peptide fragments of a target protein are identified to be determined during multiplex analysis, a targeted MRM analysis is developed for the target protein. Preferably, the targeted MRM analysis for a given target protein will identify those peptides previously selected which are the most abundant fragment ions. Each target peptide to be determined in a multiplex analysis may, therefore, have a specific MRM analysis that is developed to identify unique fragment ions of that target peptide. The multiplex analysis occurs via a concurrent MRM analysis that includes unique identifier-type peptide fragments specific for two or more target proteins in the plant tissue sample. Preferably, the multiplexed analysis will concurrently identify those target protein specific peptides demonstrating efficient ionization and fragmentation upon analysis in both the presence and absence of complex matrix. A target protein included in the multiplex analysis can be identified with one or more specific parent/daughter ion transitions pairs.

A single MS/MS multiplex analysis may then be performed for multiple target proteins in a complex protein mixture. Due to the sensitivity and selectivity of mass spectrometry, a complex protein sample to be subjected to MS/MS multiplex analysis need not be as pure or abundant as a sample to be analyzed by conventional techniques, such as immunochemistry or PCR. However, a complex protein sample to be subjected to MS/MS multiplex analysis may be prepared according to extraction conditions optimized for robust analytical performance of the multiplex method. Protein samples may be prepared according to techniques such as, inter alia, salt extraction (for example, ammonium bicarbonate), salt extraction in the presence of urea, and detergent extraction (for example, CHAPS), or other enrichment-type methodologies.

The plant material from which a multiplexed protein sample may be prepared is at the discretion of the skilled artisan. Suitable material may include, for example, tissue or cells from a transgenic plant, tissue from a plant or cells resulting from a genetic transformation procedure, tissue or cells from non-transgenic plants being analyzed for the presence of a contaminating transgene, or plant-derived materials of suspected transgenic plant origin.

MS multiplex analysis is performed on the complex protein sample. The complex protein sample is injected into an ionization chamber of the MS in which a first (parent) ion is produced. The parent ion may be detected directly in a first MS, or it may be isolated by the first MS, fragmented into characteristic daughter ions, and one or more of the daughter ions detected in a second MS (MS/MS).

Ions may be detected using several detection modes. For example, selected ions may be detected using a selective ion monitoring mode (SIM) which includes multiple reaction monitoring (MRM) or selected reaction monitoring (SRM). Alternatively, ions may be detected using a scanning mode.

The mass-to-charge ratio may be determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as a "mass filter" and "mass detector" for the ions injected into the instrument.

Collision-induced dissociation ("CID") is often used to generate the daughter ions for further detection. In CID, parent ions gain energy through collisions with an inert gas, such as argon, and subsequently fragmented by a process referred to as "unimolecular decomposition." Sufficient energy must be deposited in the parent ion so that certain bonds within the ion can be broken due to increased vibrational energy.

In MS/MS, parent ions are selected in the first MS analysis. These selected parent ions are then pass to the collision cell to generate the peptide specific daughter ions for identification and quantitation. Under a given set of ionization/fragmentation conditions, parent and daughter ions are produced in a reproducible fashion giving the MS/MS technique extremely powerful analytical capability.

The mass spectrometer typically provides the user with an ion scan; that is, the relative abundance of each m/z over a given range (e.g., 10 to 1200 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards (e.g., internal standards and external standards) can be run with the samples and a standard curve constructed based on ions generated from those standards. Using such a standard curve, the relative abundance of a given ion can be converted into an absolute amount of the original molecule. Numerous other methods for relating the presence or amount of an ion to the presence or amount of the original molecule are well known to those of ordinary skill in the art.

The choice of ionization method can be determined based on the analyte to be measured, type of sample, the type of detector, the choice of positive versus negative mode, etc. Ions can be produced using a variety of methods including, but not limited to, electron ionization, chemical ionization, fast atom bombardment, field desorption, and matrix-assisted laser desorption ionization (MALDI), surface enhanced laser desorption ionization (SELDI), desorption electrospray ionization (DESI), photon ionization, electrospray ionization, and inductively coupled plasma. Electrospray ionization refers to methods in which a solution is passed along a short length of capillary tube, to the end of which is applied a high positive or negative electric potential. Solution reaching the end of the tube, is vaporized (nebulized) into a jet or spray of very small droplets of solution in solvent vapor. This mist of droplets flows through an evaporation chamber which is heated to prevent condensation and to evaporate solvent. As the droplets get smaller the electrical surface charge density increases until such time that the natural repulsion between like charges causes ions as well as neutral molecules to be released.

The effluent of an LC may be injected directly and automatically (i.e., "in-line") into the electrospray device. In some embodiments, proteins contained in an LC effluent are first ionized by electrospray into a parent ion. The first quadropole of the MSMS is tuned to be a mass filter for the multiplexed target proteins' parent ions.

Parent ion(s) passing the first quadropole are then ionized and/or fragmented prior to passing into the second quadropole. In some embodiments, the ions are collided with a inert gas molecule in a process of collision-induced dissociation (CID). Suitable inert gases include, for example, argon, helium, nitrogen, etc. Desirably, the multiplexed target proteins' parent ions are fragmented into daughter ions that are subsequently detected.

VI. Maintaining A Transgenic Plant Variety

Methods of the present disclosure may be used to maintain the genotype of transgenic plant variety. Complex protein samples prepared from a next generation of a transgenic plant may be subjected to MSMS multiplex analysis to determine the presence or absence of a protein of interest. The complex protein samples may comprise transgenic proteins expressed in the transgenic plant. By propagating those plants wherein presence of a transgenic protein of interest is confirmed, expression of the transgenic protein of interest in successive generations is guaranteed. Similarly, those plants of a next generation wherein presence of a transgenic protein of interest cannot be confirmed may not be propagated.

VII. Screening Results Of A Plant Transformation Procedure

Methods of the present disclosure may also be used to rapidly screen the results of a plant transformation procedure in a high-throughput manner. Due to the variability in the genotype and expression characteristics in GE plants and plant cells produced by DNA recombination, plants and plant cells produced by a plant transformation procedure will not necessarily comprise the same or similar expression profiles of introduced transgenic proteins, for example, heterologous proteins. Furthermore, endogenous proteins may exhibit differentially altered expression profiles. In some embodiments of the present disclosure, complex protein samples are prepared from plants, plant tissues, or plant cells produced by a plant transformation procedure. The prepared complex protein samples may then be subjected to a multiplex MS/MS analysis. MS spectra from the different samples are then analyzed to identify those samples exhibiting desirable expression characteristics. The source plant, plant tissue, or plant cells of the identified samples may then be propagated to select for the desirable expression characteristics.

VIII. Achieving Bioconfinement Of Transgenes

Transgenes may escape a transgenic plant and become integrated into the genome of non-transgenic surrounding plants in the environment, for example, by cross-pollination. In most instances, this is undesirable. In some embodiments, methods of the present disclosure are used to achieve bioconfinement of transgenes in a transgenic plant. In these and further embodiments, complex protein samples may be prepared from plant(s), plant tissue(s), or plant cells that are at risk of being contaminated by genetic material from a transgenic plant. The prepared complex protein samples may then be subjected to a multiplex MS/MS analysis. MS spectra from the different samples are then analyzed to determine those samples containing a target transgenic protein, for example, a transgenic protein expressed in the transgenic plant. Presence of the target protein in a sample is correlated with escape of the transgene to the source plant(s), plant tissue(s), or plant cells. By destroying, confining, or otherwise limiting the growth of the contaminated plant(s), plant tissue(s), or plant cells, bioconfinement may be achieved.

Embodiments are susceptible to various modifications and alternative forms in addition to those specific Examples described in detail herein. Thus, embodiments are not limited to the particular forms disclosed. Rather, the scope of the disclosure encompasses all modifications, equivalents, and alternatives recited in the appended claims.

EXAMPLES

Example I

Six separate transgenic proteins (Cry1F, Cry34, Cry35, AAD-1, AAD-12 and PAT) were selected for development of a LC\MS\MS multiplex analysis. The individual proteins were detected and identified by mass spectroscopy in a single injection of a complex protein mixture.

The first version of the multiplex analysis was performed by proteolytically digesting the six proteins individually, and then fortifying the resulting protein peptides into proteolytically digested plant tissue extracts and using LC\MS\MS for detection of specific precursor/fragment ions for each of the six proteins in a single injection. The methodology developed during this first multiplex version was then applied towards multiplex detection of four proteins expressed in current inbred maize breeding material.

Example II

LC\MS\MS Multiplex Detection in Plant

Table 1 lists concentrations of each individual stock protein received, and the resulting dilutions of each protein upon trypsin digest. Prior to digestion with the protease trypsin, all proteins were buffer exchanged into 25 mM ammonium bicarbonate, pH 7.9 (SIGMA) to ensure efficient digestion conditions. An aliquot from each of the stock proteins (see Table 1) was transferred into a sterile 1.5 mL eppendorf tube and brought to 100 µL using 25 mM ammonium bicarbonate, pH 7.9. Zeba Desalt Spin Columns (Pierce # 89882) were used for buffer exchange of each protein as per manufacturer's recommendations. Three spin washes of the Zeba column were performed, each wash using 300 µL of 25 mM ammonium bicarbonate, pH7.9, and spinning at 1,500 g for 1 minute. The 100 µL aliquot for each sample protein was then applied to the surface of the Zeba column resin and spun at 1,500 g for 2 minutes. This buffer-exchanged material was then used directly for trypsin digestion for generation of protein peptide fragments. Initial trypsin digestion of the six proteins did not include a protocol step to alkylate cysteine amino acid residues. This alkylation step may be incorporated later, but with high throughput analysis as a goal, leaving the alkylation step out could conserve significant time and effort towards final analysis. Each 100 µL buffer-exchanged protein sample was brought to 5 mM DTT with the addition of 1 µL of 0.5 M DTT, then heat denatured at 95° C. for 20 minutes and cooled to room temperature (25° C.). Sequencing grade modified trypsin was resuspended in 25 mM ammonium bicarbonate, pH7.9, to a concentration of 0.4 µg/µL. Trypsin enzyme was added to each protein sample for a final enzyme to substrate ratio range of 1:20 to 1:50. Trypsin digestion was performed in a thermocycler using a temperature profile of 37° C. for 16 hours, then cooled to 4° C. After trypsin digestion, 3 µL of 10% formic acid was added to each protein digest.

TABLE 1

Protein concentrations and dilutions for each LC\MS\MS Multiplex-6 protein trypsin digest.

| Name | [stock] ug/ml | vol. stock digested (ml) | trypsin digest amount protein digested (ug's) | 100 ul final digest volume dil. factor from digest | [trypsin dig.] [protein] of digest (ug/ml) |
|---|---|---|---|---|---|
| Cry1F | 160 | 0.01 | 1.6 | 1:10 | 16 |
| Cry34 | 500 | 0.025 | 12.5 | 1:4 | 125 |
| Cry35 | 187 | 0.045 | 8.415 | 1:2.2 | 85.0 |
| AAD-1 | 4200 | 0.005 | 21 | 1:20 | 210 |
| AAD-12 | 1000 | 0.02 | 20 | 1:5 | 200 |
| PAT | 300 | 0.033 | 9.9 | 1:3 | 100 |

Initially, each of the six trypsin digested protein samples were individually analyzed via ESI– LC\MS\MS to determine tryptic peptide fragments that would provide the detection sensitivity and specificity for simultaneous multiplex identification of all six proteins in a single analysis. The mass spectrometer used for method development was an Applied Biosystems MDS Sciex 4000 Q Trap hybrid triple quad, (Foster City, Calif. model # 1004229-V) utilizing a Turbo V ESI source housing fitted with a TSI probe. The samples were introduced into the mass spectrometer via an Agilent 1100 HPLC system. Table 2 includes specific model number and firmware version information for the different instrumentation components.

TABLE 2

Model/Firmware version information for instrument components.

| | |
|---|---|
| Mass Spectrometer | 4000 Q TRAP |
| Firmware Version | M401402 B4T0301 M3L1412 B3T0300 |
| Component Name | Linear Ion Trap Quadrupole LC/MS/MS Mass Spectrometer |
| Component ID | 4000 Q TRAP |
| Manufacturer | AB Sciex Instruments |
| Model | 1004229-V |
| AutoSampler | Agilent 1100 G1367A |
| Firmware Version | A.05.04 |
| Linked Pump | G1312A |
| Column Oven | Agilent 1100 G1316A |
| Firmware Version | A.05.05 |
| Switching Valve | Installed |
| Pump | Agilent 1100 G1312A |
| Firmware Version | A.05.04 |

Reverse phase chromatography was performed using an Agilent 1100 HPLC system equipped with a Phenomenex Jupiter Proteo 50×20 mm 4 µM column with a loading condition of 95% A ($H_2O$/0.1% formic acid)/5% B (acetonitrile/0.1% formic acid) for 1 minute, and with a gradient to 90% B in 20 minutes. The column was regenerated with a 2 minute hold at 90% B, and then re-equilibrated to 5% B for 5 minutes. For initial screening of individual protein peptides, approximately 10-50 fmol of each protein was loaded onto the column for analysis.

An IDA acquisition method incorporating two EPI scans to be performed on the two most abundant ions detected from a list of MRM transitions specific for each protein was performed on each of the six proteins to be multiplexed. This fragmentation data was informative on selecting the fragment ions demonstrating highest abundance from each peptide detected. Generally, the top three fragment ions from a detected precursor peptide were selected for further method development. For this IDA acquisition, the Sciex 4000 Q TRAP incorporated the following conditions: IS voltage 5500, DP 75, EP 10, CXP 12, CUR 10, CAD HIGH, TEM 450, GS1 35, GS2 35, RES Q1 unit, and RES Q3 unit. The CE values for each peptide were empirically tested with an optimal value used for each peptide. Using the peptide fragmentation data accumulated from the individual IDA analysis on each of the six proteins, an MRM analysis was then performed on each individual protein to identify the precursor ions from each protein with good ionization efficiencies. For each multiplex protein a MRM list of all tryptic peptides was used to create an individual MRM analysis method. Using the individual protein MRM analysis data as a measure for ionization efficiency, peptides were chosen for each protein to serve as precursor ions in a multiplex format. The multiplex peptides are listed in Table 3.

TABLE 3

Peptides selected for initial multiplex-6 LC/MS/MS method.

| | Protein/Multiplexed peptides | |
|---|---|---|
| | AAD-1((R)-2,4-dichlorophenoxypropionate dioxygenase) | |
| T6 | FGPVDPVPLLK | (SEQ ID NO: 1) |
| T7 | SIEGYPEVQMIR | (SEQ ID NO: 2) |
| T12 | VFGSLYQAQNR | (SEQ ID NO: 3) |
| | AAD-12 ((S)-2,4-dichlorophenoxypropionate/alpha-ketoglutarate dioxygenase) | |
| T4 | IGGGDIVAISNVK | (SEQ ID NO: 4) |
| T9 | AAYDALDEATR | (SEQ ID NO: 5) |
| T19 | AEPWDFK | (SEQ ID NO: 6) |
| | Cry1F (Pesticidal crystal protein cry1Fa (Insecticidal delta-endotoxin Cry1F(a))) | |
| T22 | TYPIQTSSQLTR | (SEQ ID NO: 7) |
| T46 | IFAGQFNK | (SEQ ID NO: 8) |
| | Cry34 (crystal protein ET79 [Bacillus thuringiensis]) | |
| T7 | TSPTNVANDQIK | (SEQ ID NO: 9) |
| | Cry35 (Cry35Ab-like [Bacillus thuringiensis]) | |
| T9 | VLTAGTGQALGLIR | (SEQ ID NO: 10) |
| T17 | YQYWQR | (SEQ ID NO: 11) |
| | PAT (Phosphinothricin N-acetyltransferase (PPT N-acetyltransferase)) | |
| T2 | TEPQTPQEWIDDLER | (SEQ ID NO: 12) |
| T8 | LGLGSTLYTHLLK | (SEQ ID NO: 13) |
| T10 | SVVAVIGLPNDPSVR | (SEQ ID NO: 14) |

Example III

A single LC\MS\MS multiplex targeted MRM analysis for all six DAS proteins was then created using the precursor/fragment ion data generated from individual protein analysis. These peptides were first LC\MS\MS multiplex detected by fortifying ammonium bicarbonate buffer (25 mM, pH7.9) with trypsin-digested material from each of the six proteins. Approximately 5-20 fmol of each protein was injected onto the column for initial multiplex-6 analysis of the fortified buffer.

Figure 1B:
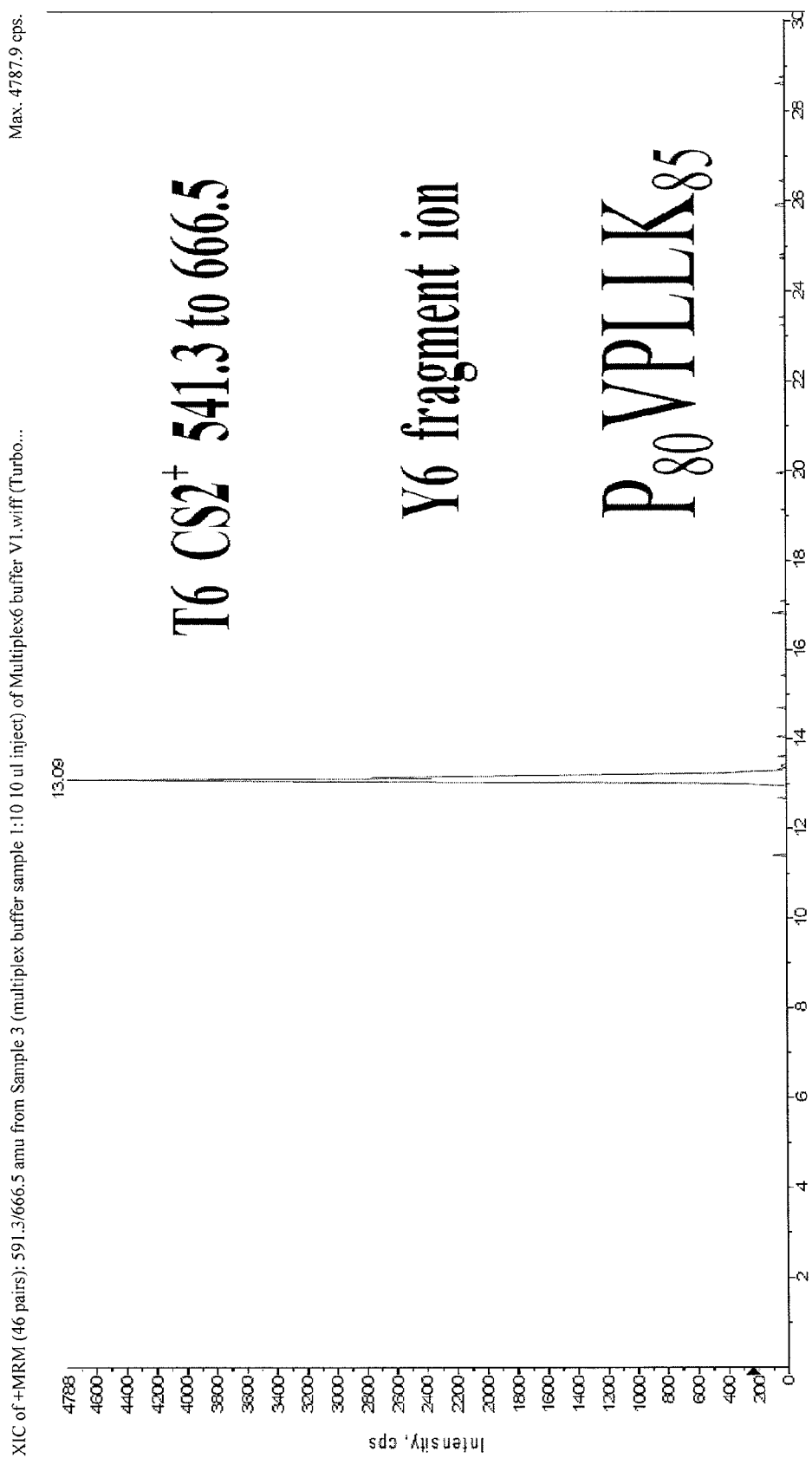
FIG. 1b includes detection of T6 peptide Y6 fragment ion PVPLLK (SEQ ID NO:16).
Figure 1C:
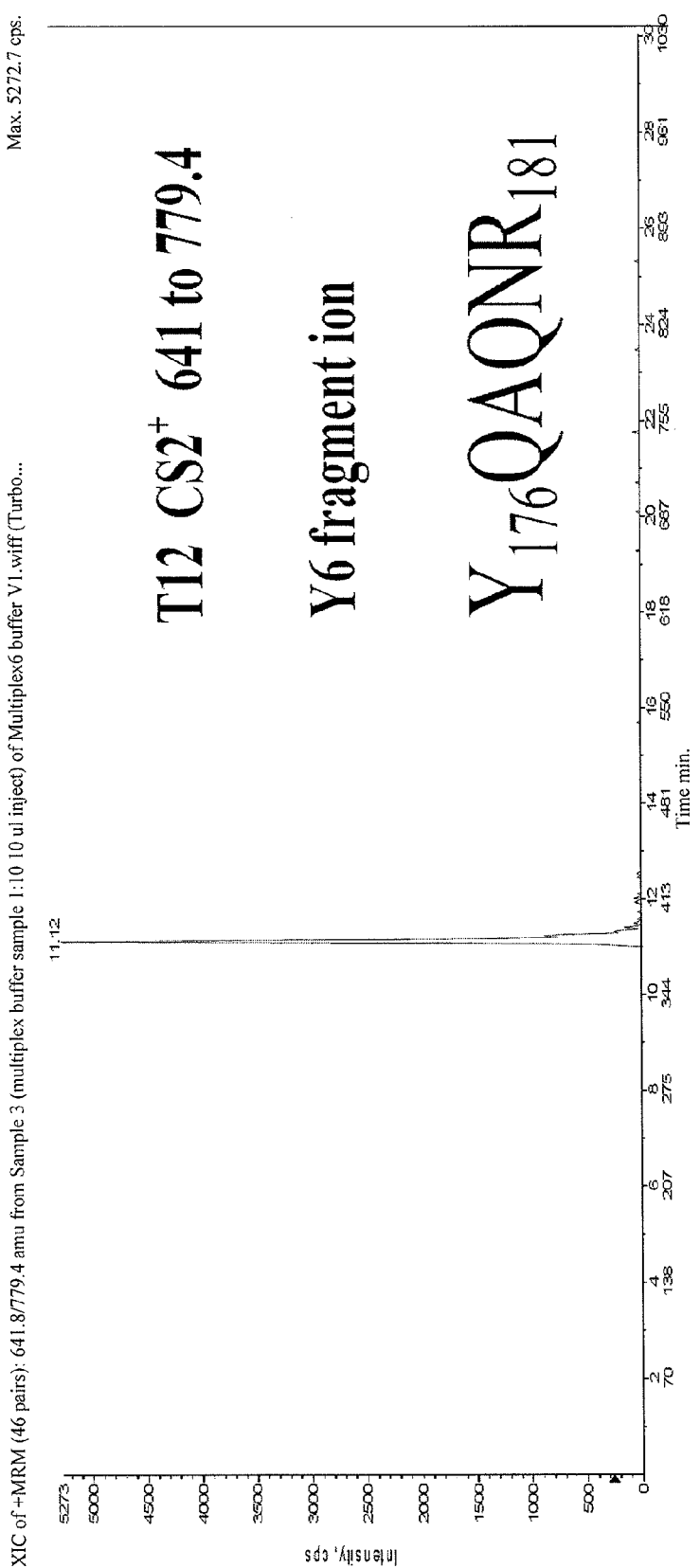
FIG. 1c includes detection of T12 Y6 fragment ion YQAQNR (SEQ ID NO:17).

FIGS. 1-6 show extracted ion chromatograms for each of the six proteins detected in a single injection. Specifically, FIG. 1 shows LC\MS\MS multiplex detection of AAD-1. The data is an extracted LC\MS\MS ion chromatogram for AAD-1 ((R)-2,4-dicholorophenoxypropionate dioxygenase), detected in a single injection with AAD-12, Cry1F, Cry34, Cry35, and PAT in maize seed extract.

Figure 2A:
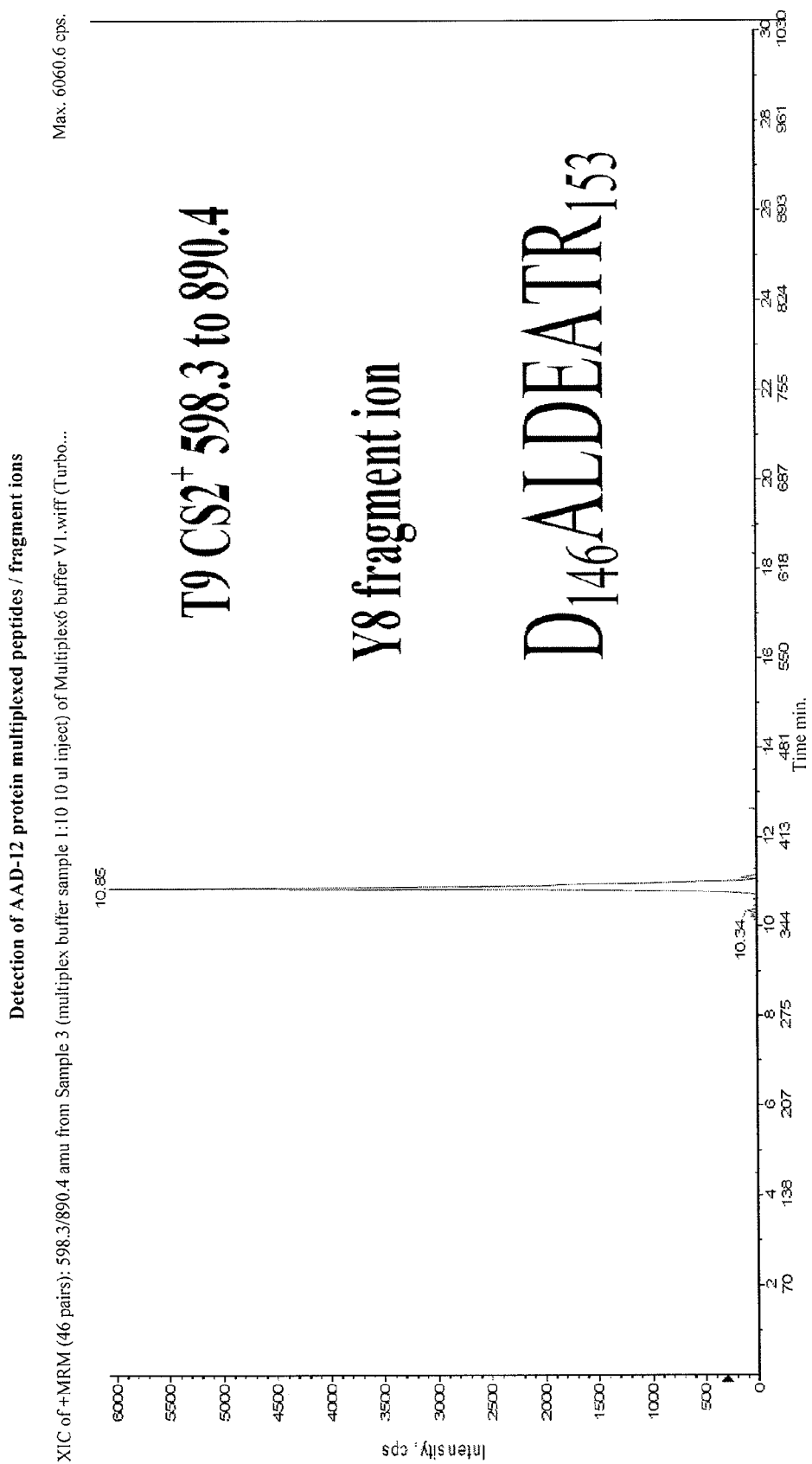
FIG. 2a includes detection of T9 peptide Y8 fragment ion DALDEATR (SEQ ID NO:18).
Figure 2B:
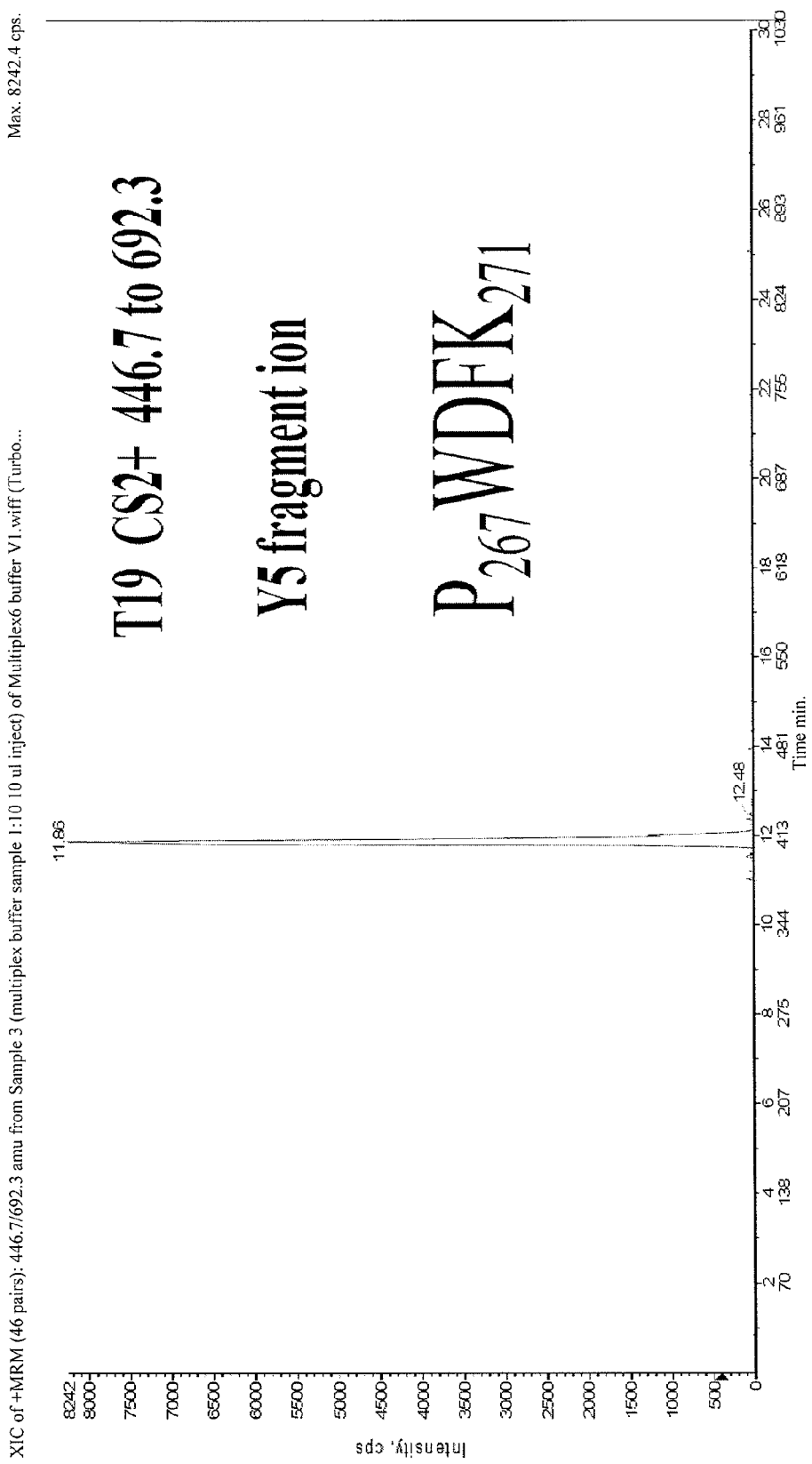
FIG. 2b includes detection of T19 peptide Y5 fragment ion PWDFK (SEQ ID NO:19).
Figure 2C:
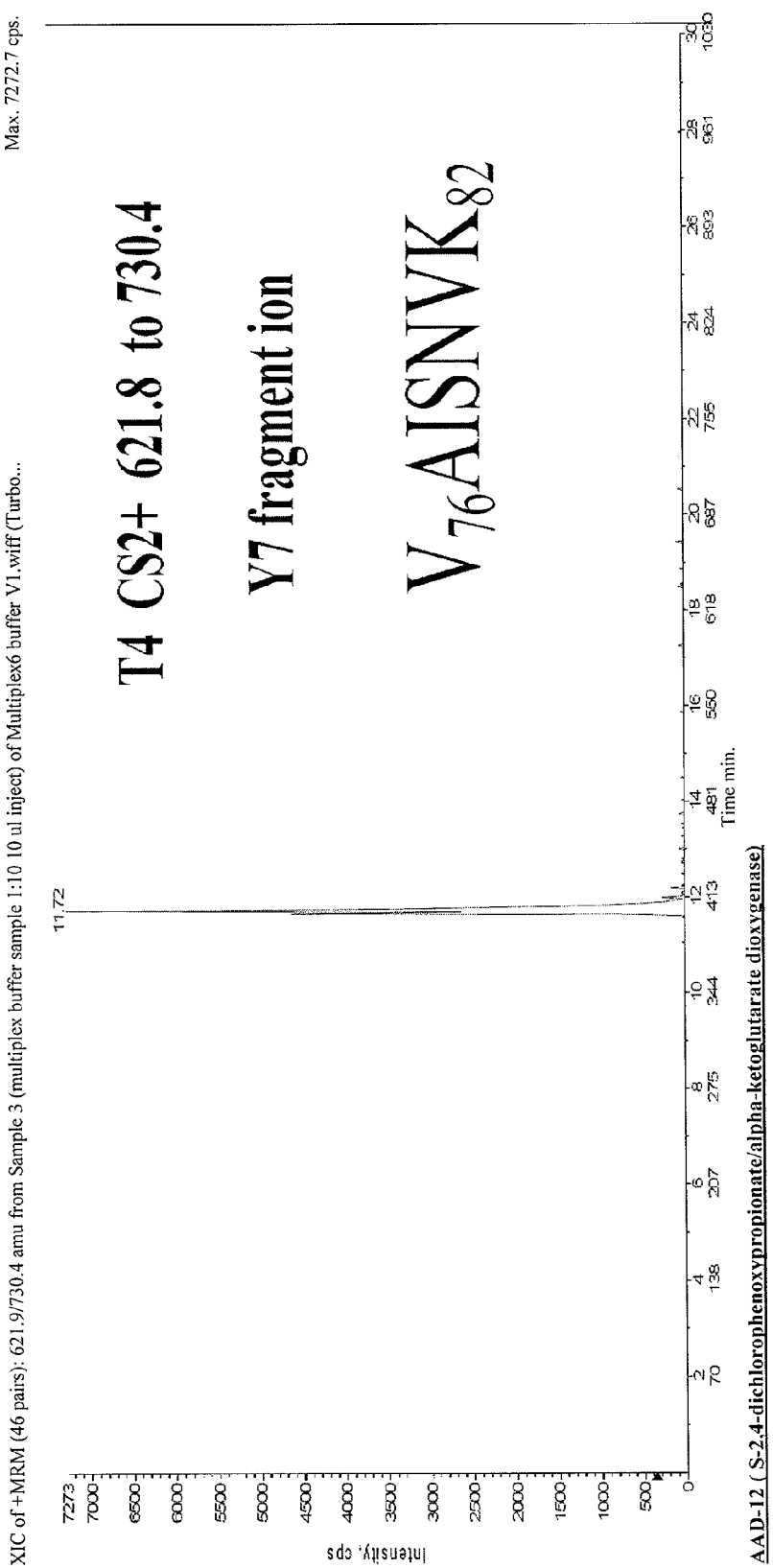
FIG. 2c includes detection of T4 peptide Y7 fragment ion VAISNVK (SEQ ID NO:20).
Figure 3A:
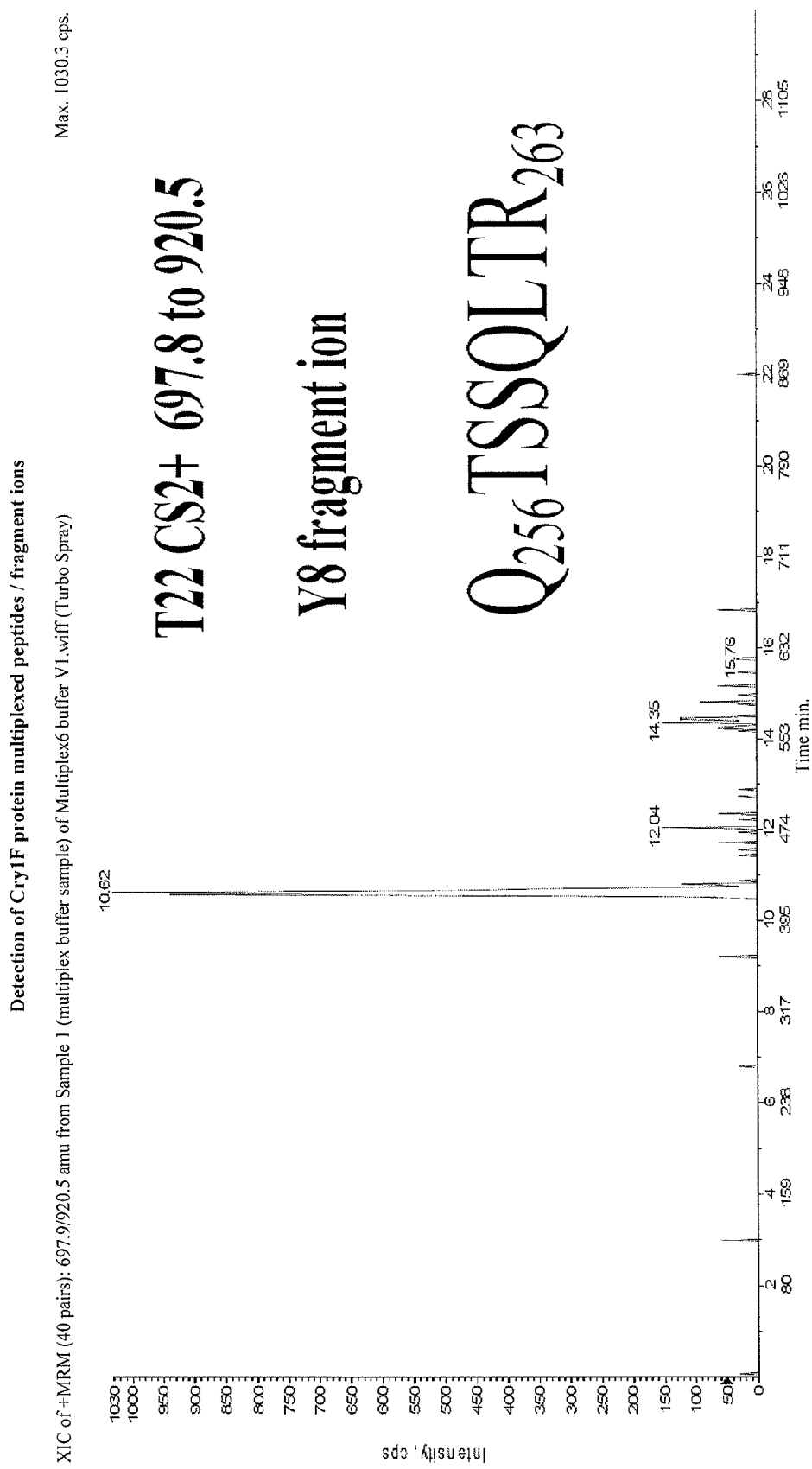
FIG. 3a includes detection of T22 peptide Y8 fragment ion QTSSQLTR (SEQ ID NO:21).
Figure 3B:
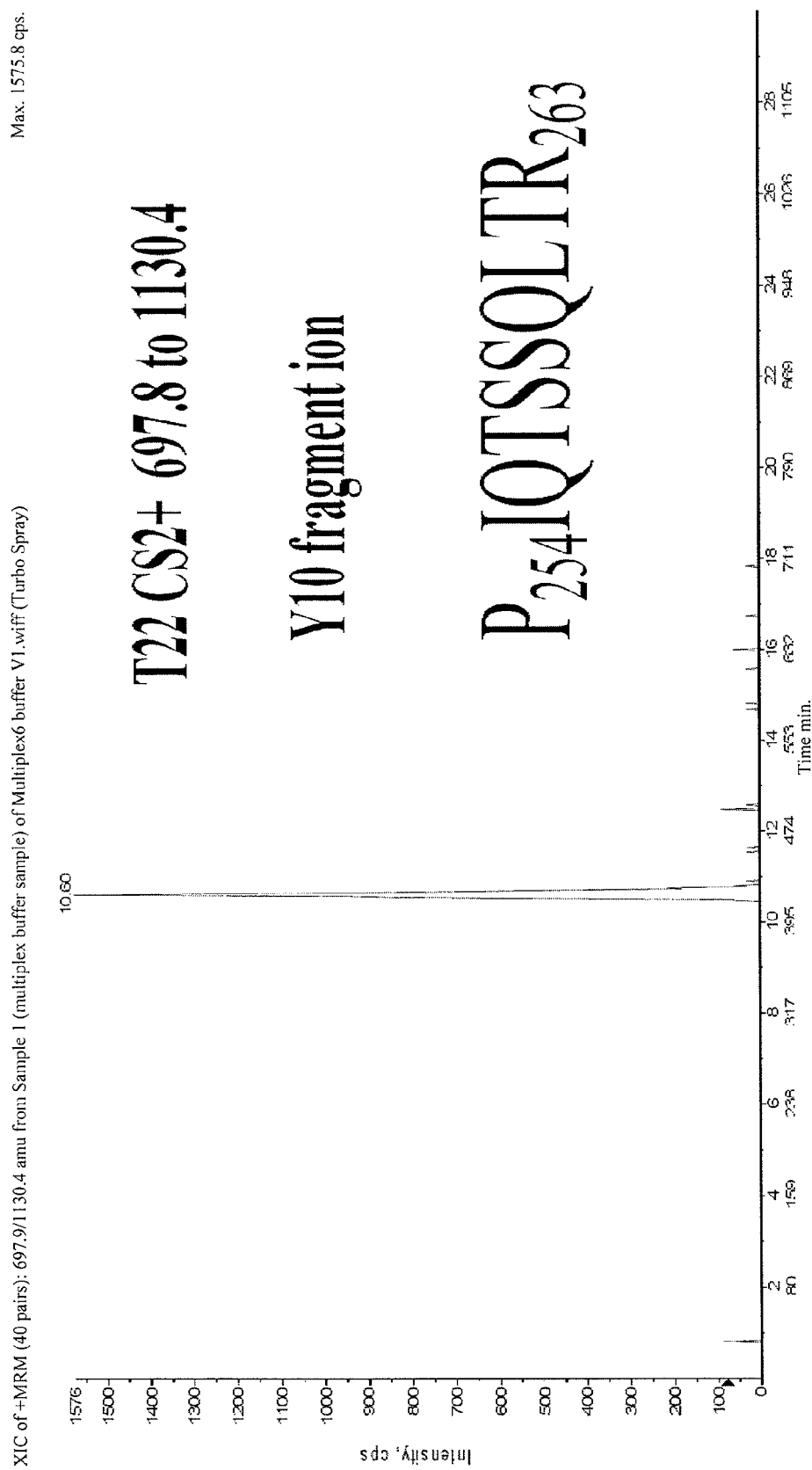
FIG. 3b includes detection of T22 peptide Y10 fragment ion PIQTSSQLTR (SEQ ID NO:22).
Figure 3C:
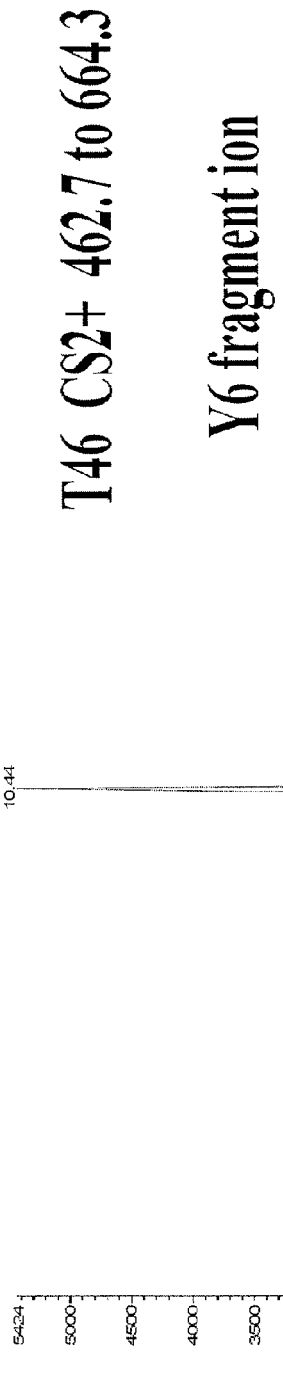
FIG. 3c includes detection of T46 peptide Y6 fragment ion AGQFNK (SEQ ID NO:23).
Figure 3C:
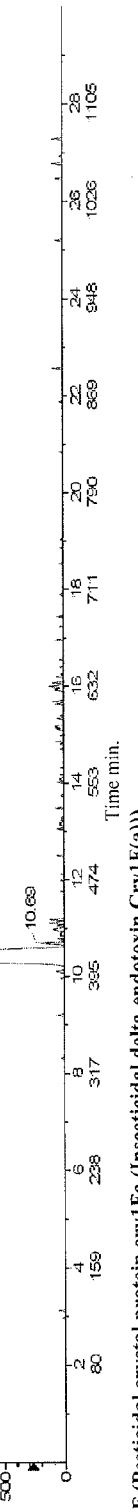

FIG. 2 shows LC\MS\MS multiplex detection of AAD-12. The data is an extracted LC\MS\MS ion chromatogram for AAD-12 ((S)-2,4-dichlorophenoxypropionate/alpha-ketoglutarate dioxygenase), detected in a single injection with AAD-1, Cry1F, Cry34, Cry35, and PAT in maize seed extract.

FIG. 3 shows LC\MS\MS multiplex detection of Cry1F. The data is an extracted LC\MS\MS ion chromatogram for Cry1F (Pesticidal crystal protein cry1Fa (Insecticidal delta-endotoxin Cry1F(a))), detected in a single injection with AAD-1, AAD-12, Cry34, Cry35, and PAT in maize seed extract.

Figure 4A:
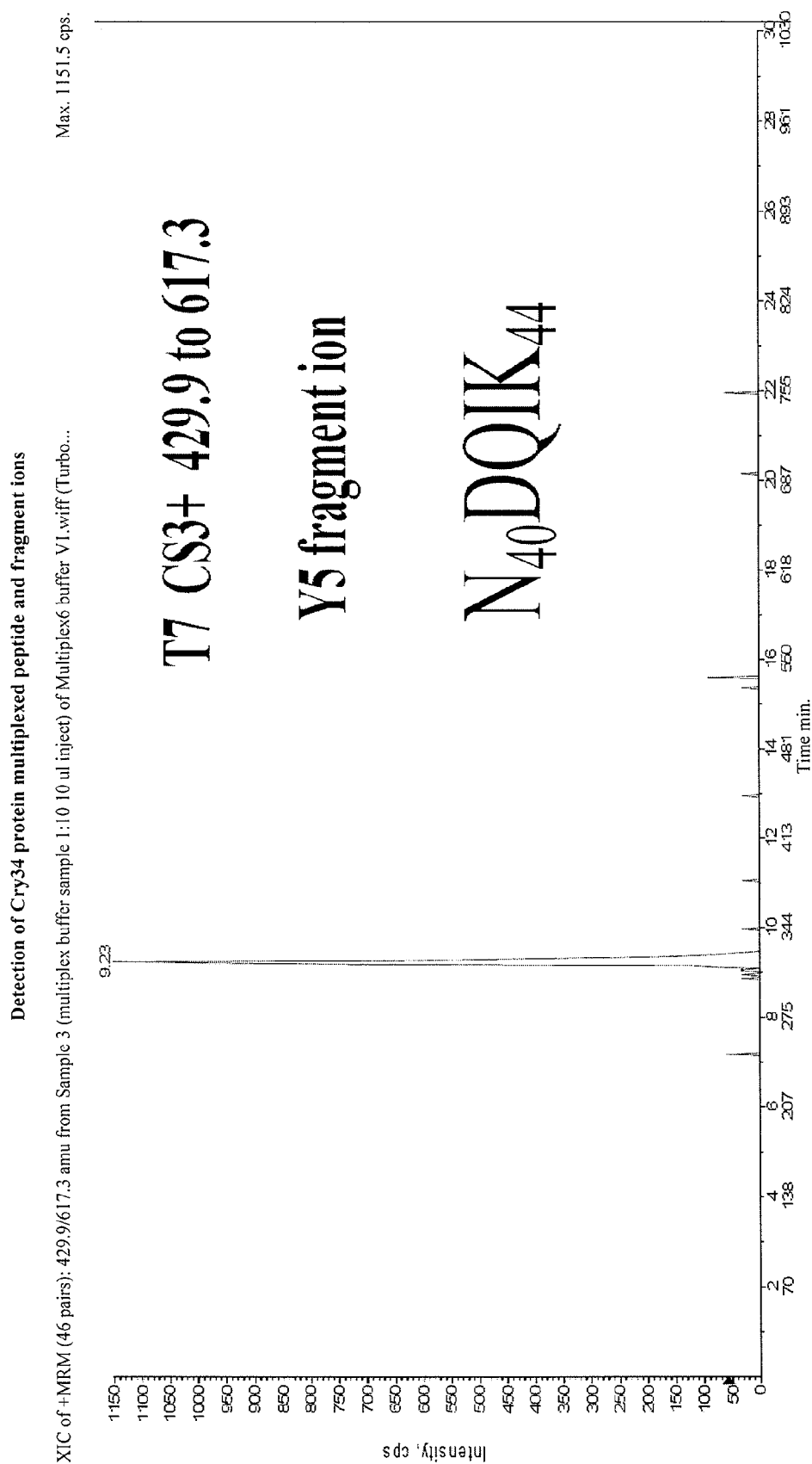
FIG. 4a includes detection of T7 peptide Y5 fragment ion NDQIK (SEQ ID NO:24).
Figure 4B:
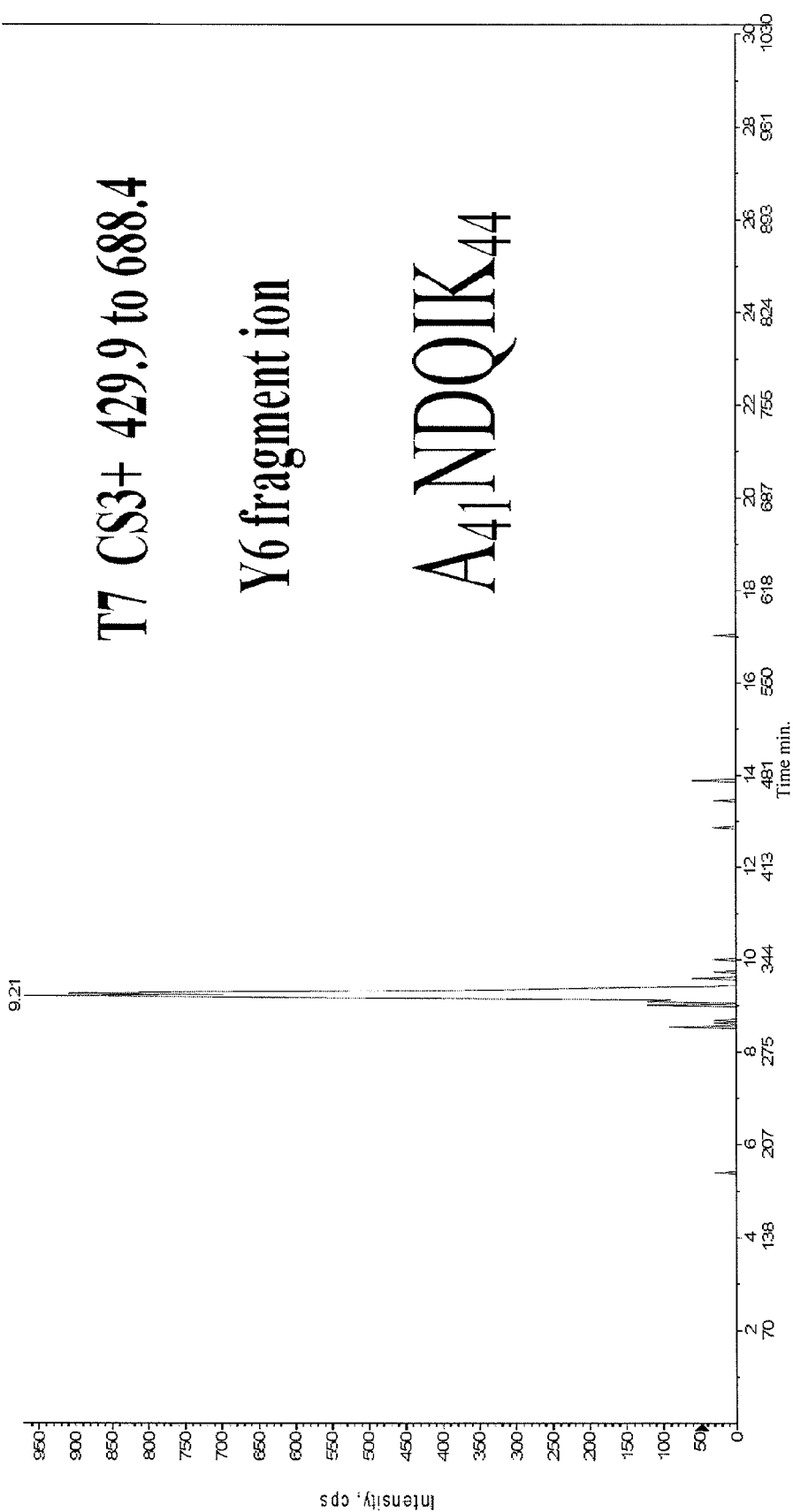
FIG. 4b includes detection of T7 peptide Y6 fragment ion ANDQIK (SEQ ID NO:25).
Figure 4C:
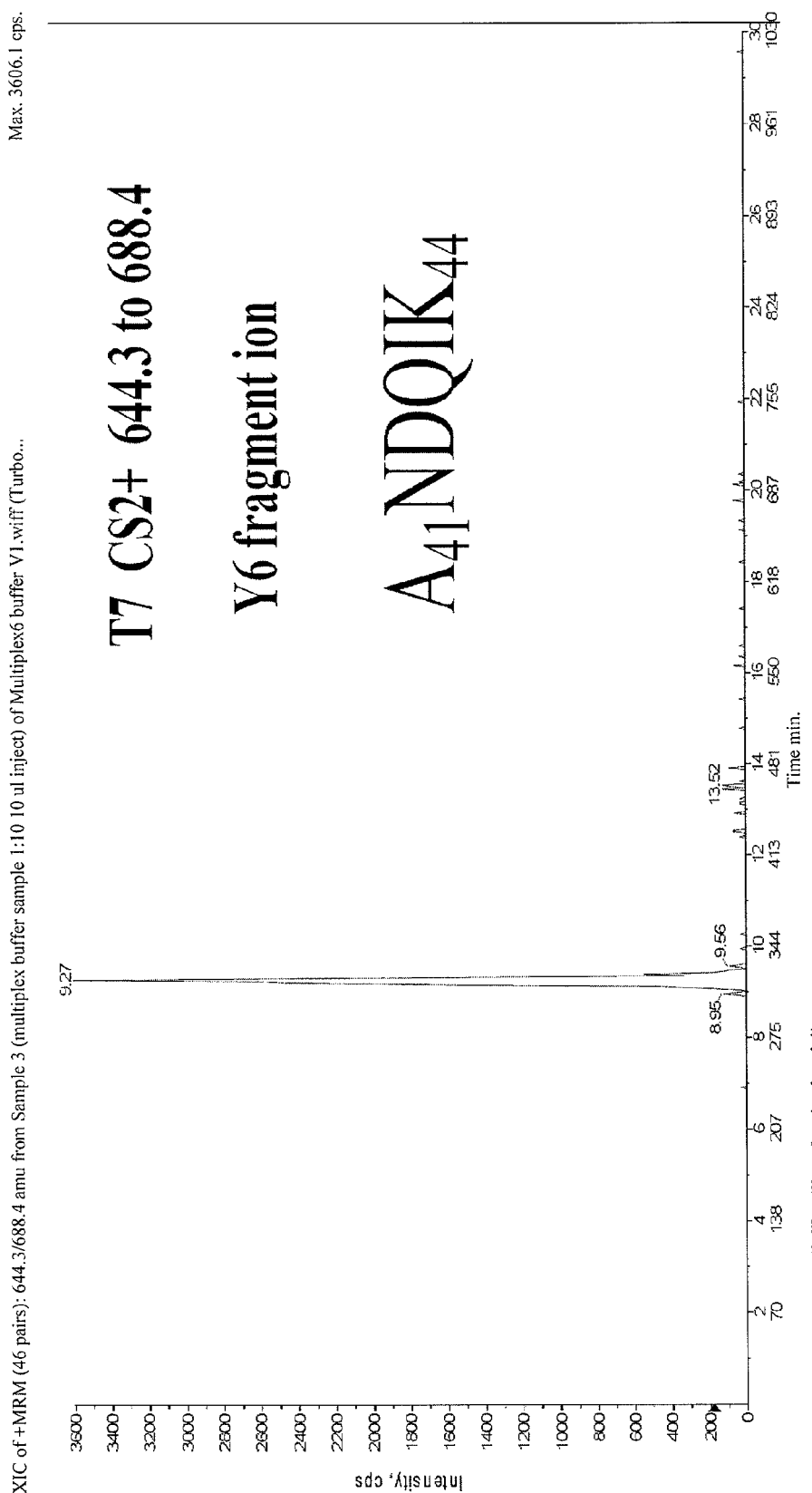
FIG. 4c includes detection of T7 peptide Y6 fragment ion ANDQIK (SEQ ID NO:25).

FIG. 4 shows LC\MS\MS multiplex detection of Cry34. The data is an extracted LC\MS\MS ion chromatogram for Cry34 (crystal protein ET79 [*Bacillus thuringiensis*]), detected in a single injection with AAD-1, AAD-12, Cry1F, Cry35, and PAT in maize seed extract.

Figure 5A:
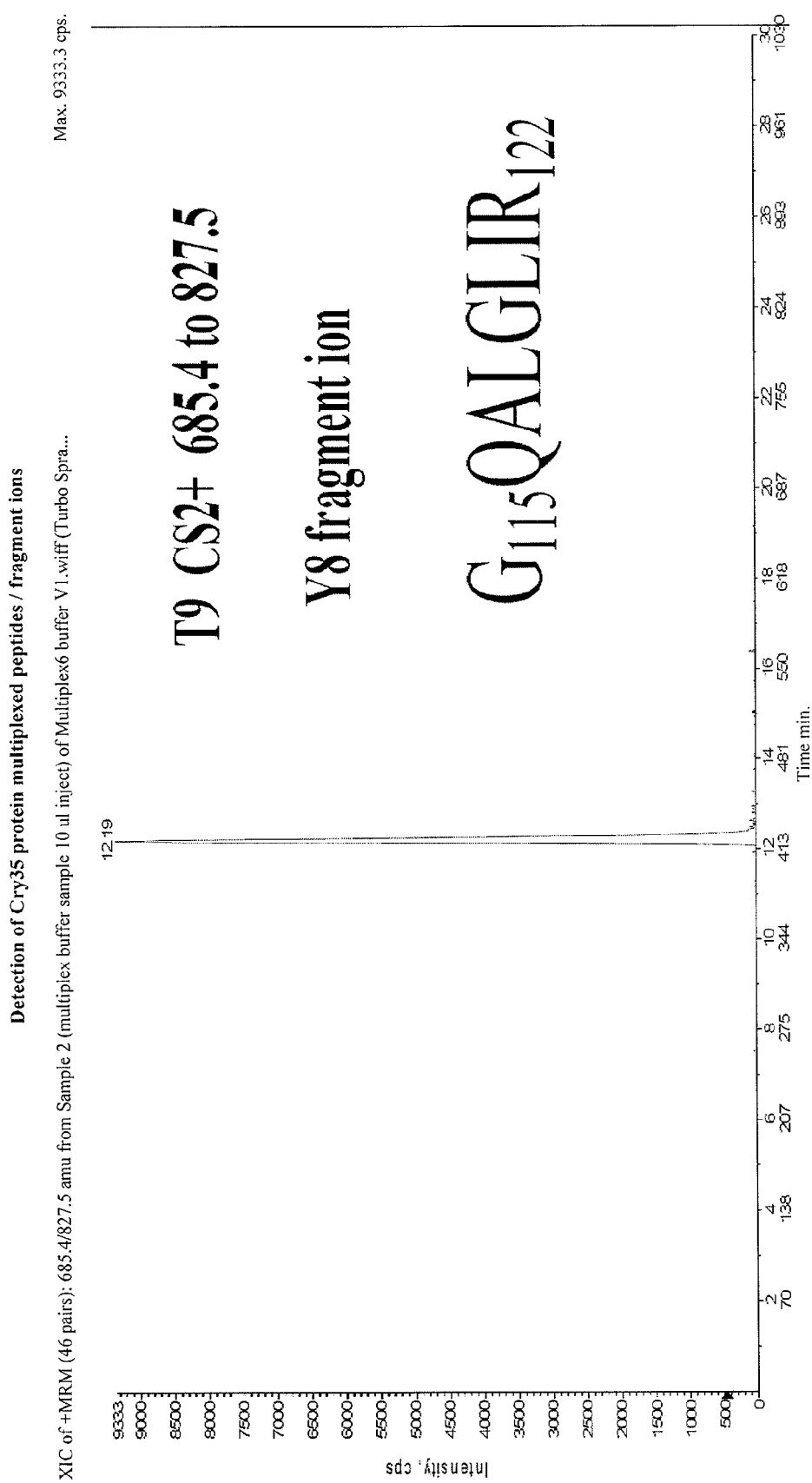
FIG. 5a includes detection of T9 peptide Y8 fragment ion GQALGLIR (SEQ ID NO:26).
Figure 5B:
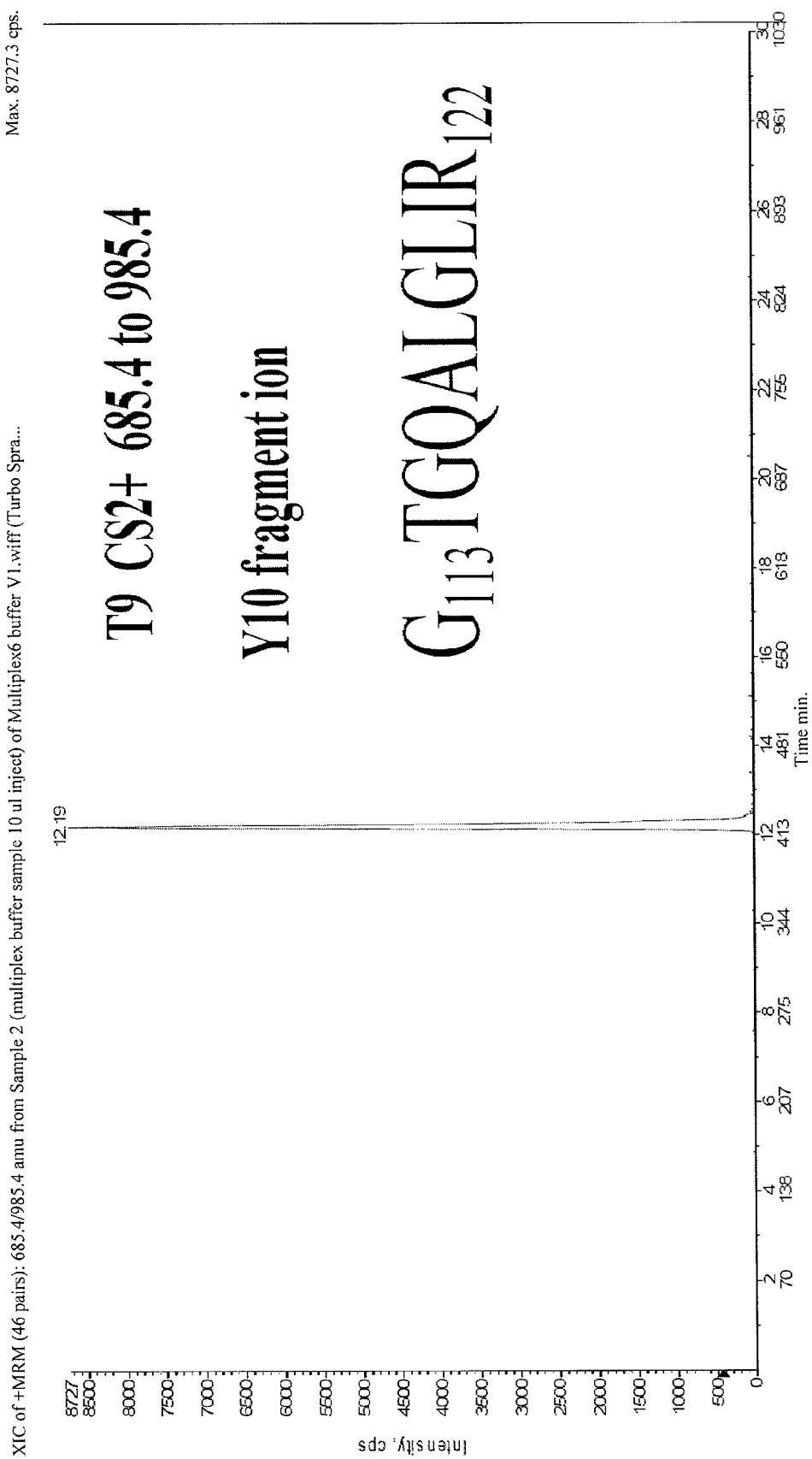
FIG. 5b includes detection of T9 peptide Y10 fragment ion GTGQALGLIR (SEQ ID NO:27).
Figure 5C:
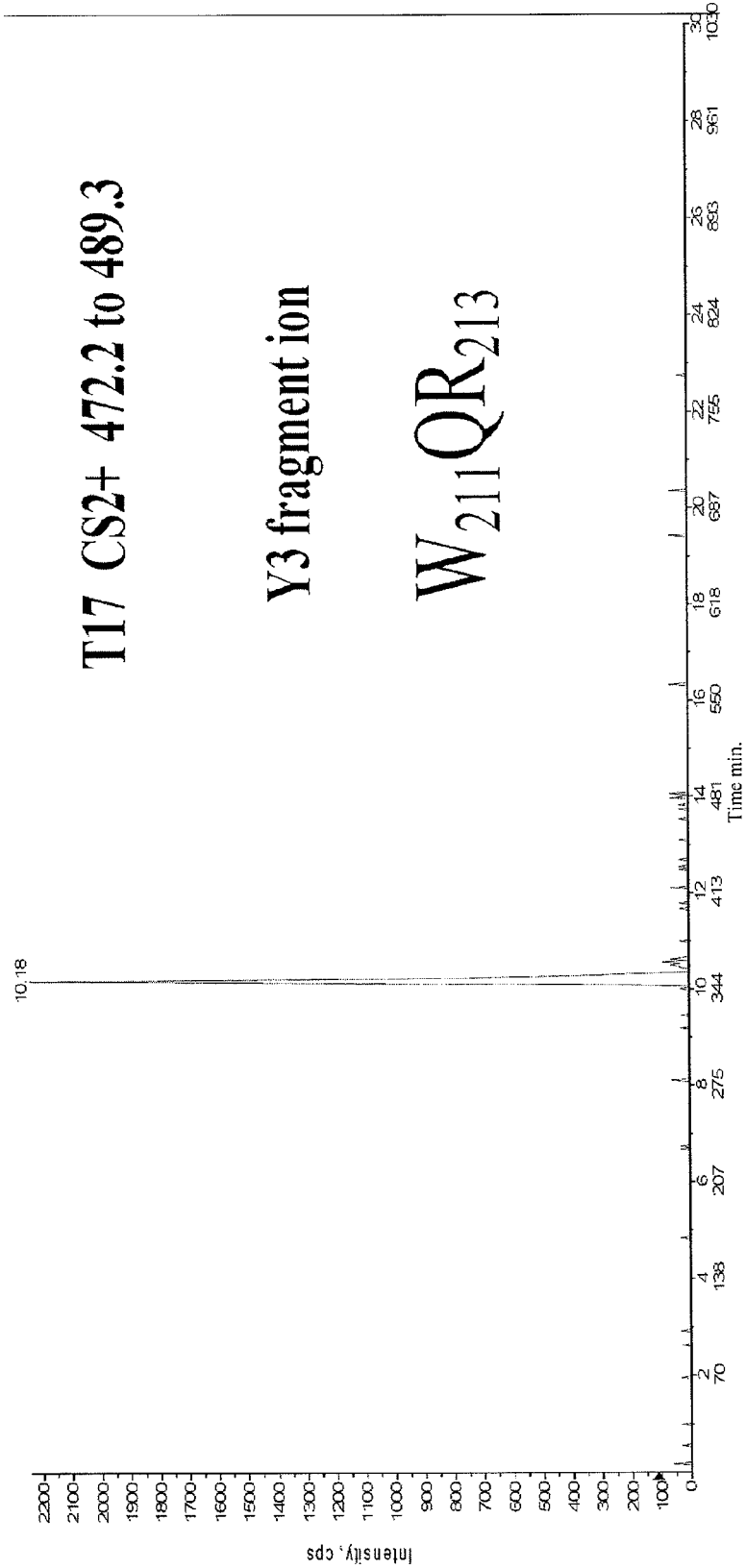
FIG. 5c includes detection of T17 peptide Y3 fragment ion WQR.

FIG. 5 shows LC\MS\MS multiplex detection of Cry35. The data is an extracted LC\MS\MS ion chromatogram for Cry35 (Cry35Ab-like [*Bacillus thuringiensis*]), detected in a single injection with AAD-1, AAD-12, Cry1F, Cry34, and PAT in maize seed extract.

Figure 6A:
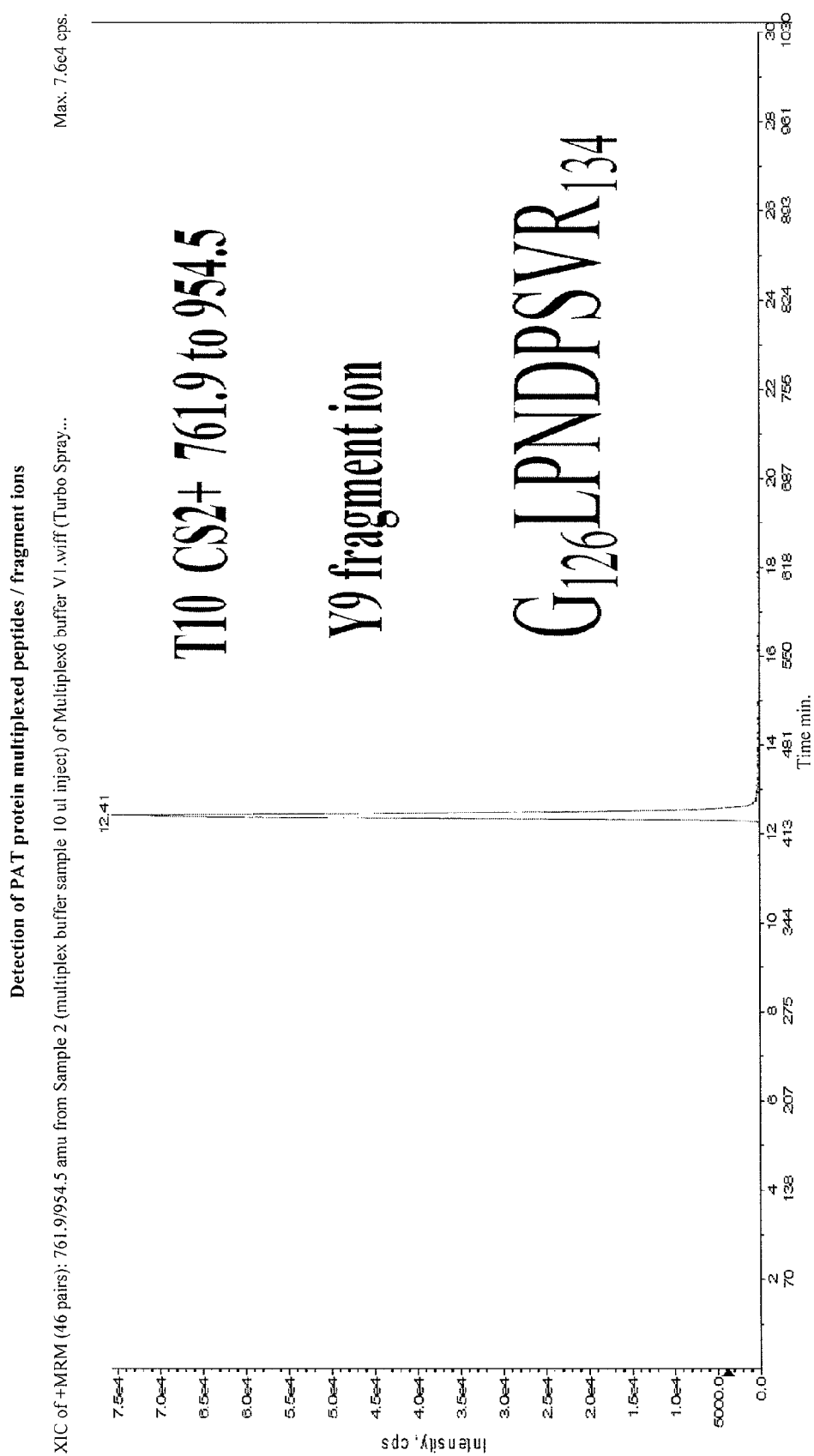
FIG. 6a includes detection of T10 peptide Y9 fragment ion GLPNDPSVR (SEQ ID NO:28).
Figure 6B:
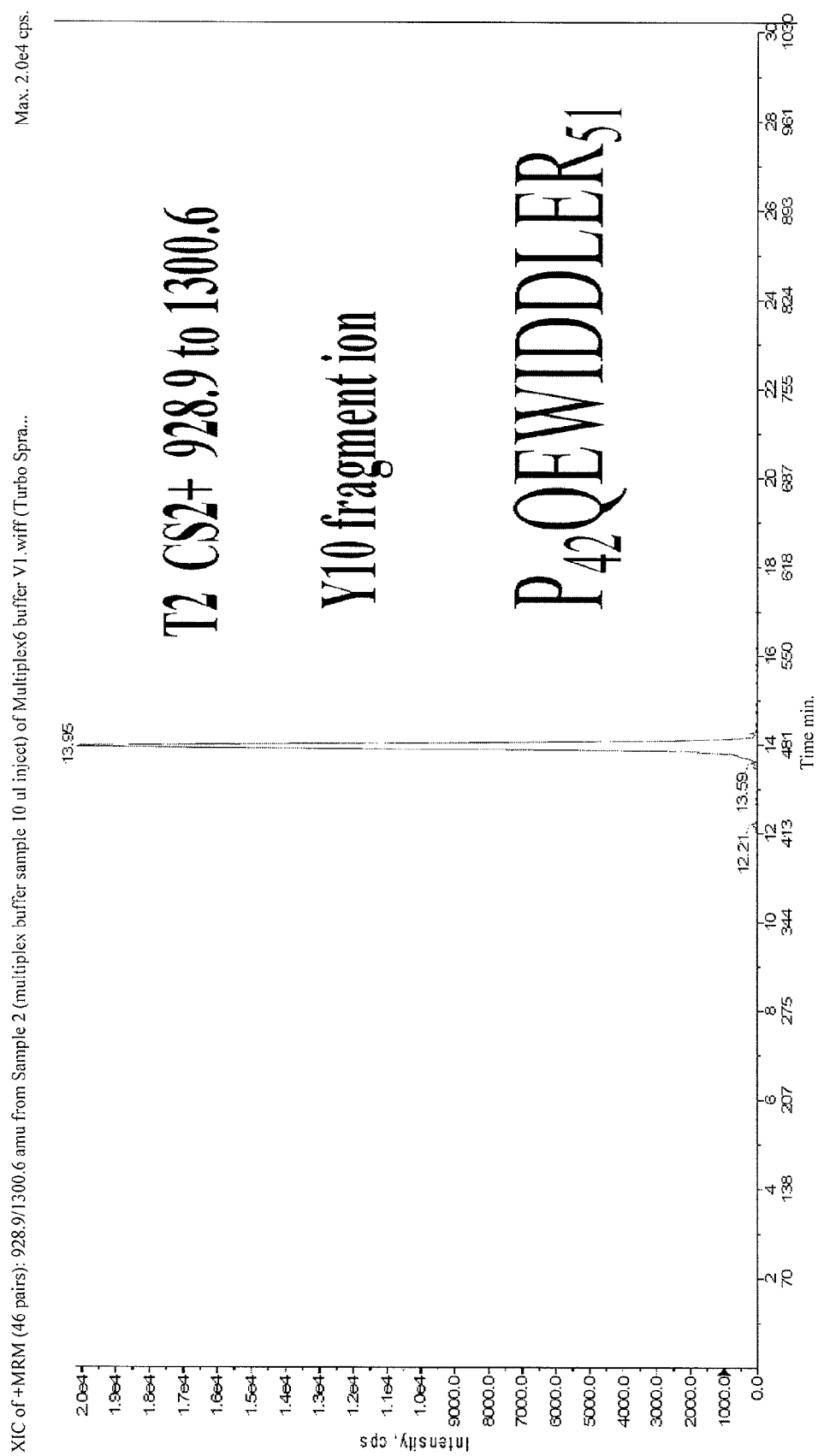
FIG. 6b includes detection of T2 peptide Y10 fragment ion PQEWIDDLER (SEQ ID NO:29).
Figure 6C:
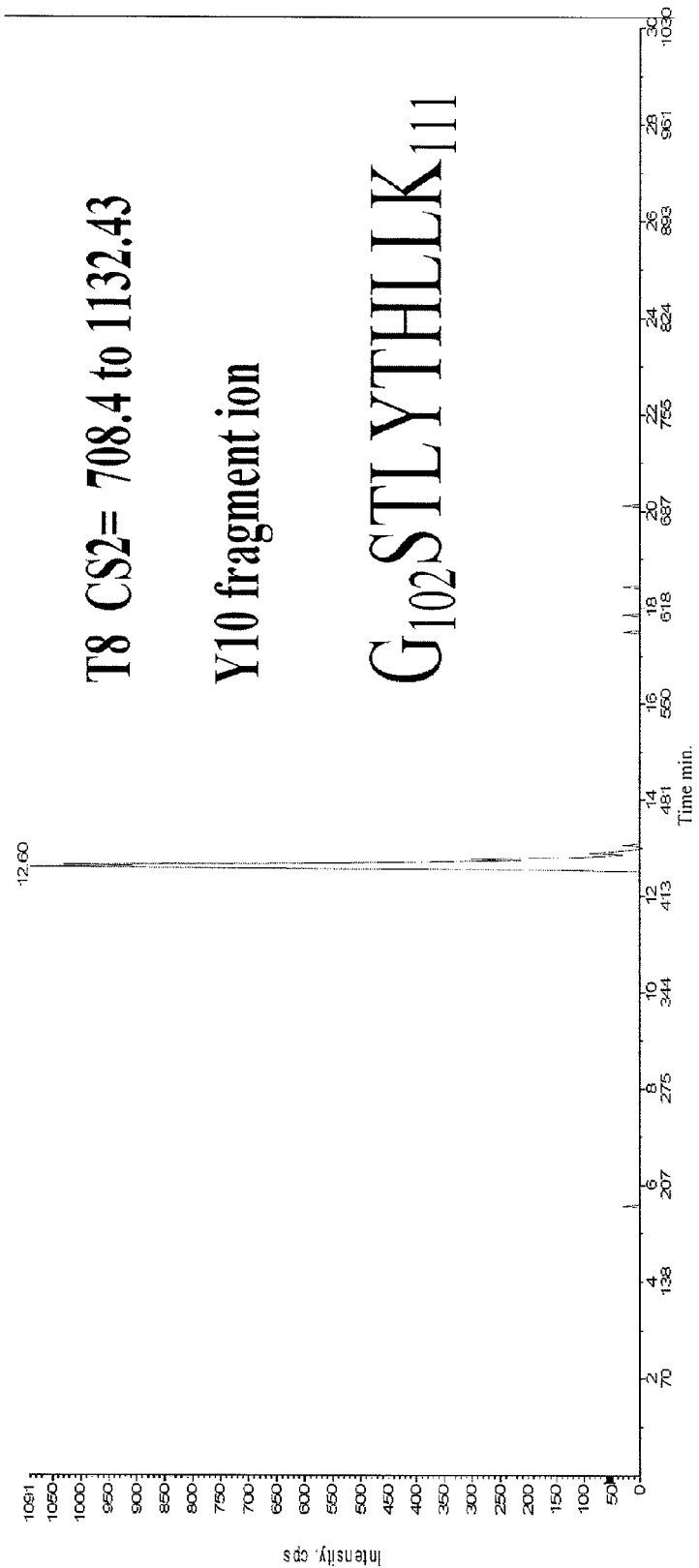
FIG. 6c includes detection of T8 peptide Y10 fragment ion GSTLYTHLLK (SEQ ID NO:30).

FIG. 6 shows LC\MS\MS multiplex detection of PAT. The data is an extracted LC\MS\MS ion chromatogram for Cry35 (Phosphinothricin N-acetyltransferase (PPT N-acetyltransferase)), detected in a single injection with AAD-1, AAD-12, Cry1F, Cry34, and Cry35 in maize seed extract.

After confirming LC\MS\MS multiplex detection of all six proteins, the ammonium bicarbonate peptide mixture was diluted into a protease digested extract from maize seed tissue for detection in seed matrix. The seed tissue used was from current inbred material. The fortified sample was diluted 1:10 in ammonium bicarbonate and then 1:2 into maize seed extract with approximately 0.2 to 1 fmol of each protein being injected onto the column and detected using the LC\MS\MS multiplex method.

Example IV

Four separate transgenic proteins (Cry1, Cry34, Cry35 and PAT) were detected and identified by mass spectroscopy in a single injection of a complex protein sample from inbred plant materials (5XH751XT). Protein was detected in both leaf and seed tissue.

The multiplex-6 methodology listed above was used to detect the presence of four separate transgenic proteins (Cry1F, Cry34, Cry35, and PAT) in a single injection of a complex protein sample from inbred line plant material (5XH751XT). In this effort, a single injection multiplex-4 method was developed to measure presence of the four proteins in both maize seed and maize leaf tissue. Experimental controls involved comparison to null 5XH751 extract spiked with whole transgenic proteins prior to digestion, and comparison to digested null 5XH751 extract.

For this experiment, consideration was also given to extraction methodology required for robust analytical performance of the multiplex method. Since multiplex detection is simultaneously measuring multiple proteins from each individual sample, the protein extraction method used needs to be efficient for all proteins for accurate measurement. As shown in FIG. 11, extraction conditions were tested on both maize leaf and seed tissue. Three separate extraction conditions were tested in an attempt to begin to understand how these four different proteins would perform in respect to finding a single extraction method to accommodate factors such as protein stability, solubility, hydrophobicity.

The appeal of a simple ammonium bicarbonate protein extraction is the ability to go directly from the extraction step to protease digestion without concern for signal suppression due to a buffer component during MS analysis. This could reduce cost, but more importantly reduce prep time and possible variability incurred during buffer exchange. The 8M urea buffer was tested to determine if a harsh solubilization method was required for detecting all four proteins in plant tissues. The PBS-T was used as this is conventional to ELISA detection methods.

5XH751XT leaf tissue: Leaf tissue was collected from a V6-V7 greenhouse plant and ground under liquid nitrogen. Each leaf sample test weight was 1.5 g. Each extraction buffer (FIG. 11) was tested at a 2:1 buffer/sample ratio (3 mL). Samples were vortexed for 2 minutes, then spun for 2 minutes, and supernatants collected.

5XH751XT seed tissue: Mature seed tissue was obtained and pulverized in a ball grinder. Each seed sample test weight was 1.5 g. Each extraction buffer (FIG. 11) was tested at a 2:1 buffer/sample ratio (3 mL). Samples were vortexed for 2 minutes, then spun for 2 minutes and supernatants collected.

Samples extracted in 8M urea or PBS-T were buffer exchanged into 25 mM ammonium bicarbonate using Pierce Zeba spin filters. For all samples, 50 μL of tissue extract was trypsin digested with 10 μg trypsin (remove) in 110 μL total volume ammonium bicarbonate. Protein digestion was performed at 37° C. for 16 h then cooled to 4° C. To serve as a positive control for each of the four proteins to be multiplex detected, a cocktail mix containing approximately 50 μg/mL of each individual whole protein was made using purified protein standards. A final 1:10 dilution of the cocktail was made into both a null leaf extract sample and a null seed extract sample for a matrix positive control concentration of approximately 5 μg/mL. These fortified nulls served as positive controls yielding accurate peptide LC retention times and MS/MS sequence fragmentation data when compared to null tissue controls (negative control) and the 5XH751XT maize tissue extractions. Since all four proteins to be multiplexed detected in 5XH751XT were proteins also used to develop the above multiplex-6 LC/MS/MS method, no further development was required for determining which protein specific peptides/fragment ions to detect and under which instrumentation conditions.

The multiplex-6 method described above was used to analyze the 5XH751XT leaf and seed tissue extracts. FIGS. 7-10 are a subset of the data acquired using multiplex-4 LC-MS/MS single injection analysis to detect Cry1F, Cry34, Cry35 and PAT proteins expressed in inbred maize leaf and seed tissue.

Figure 7A:
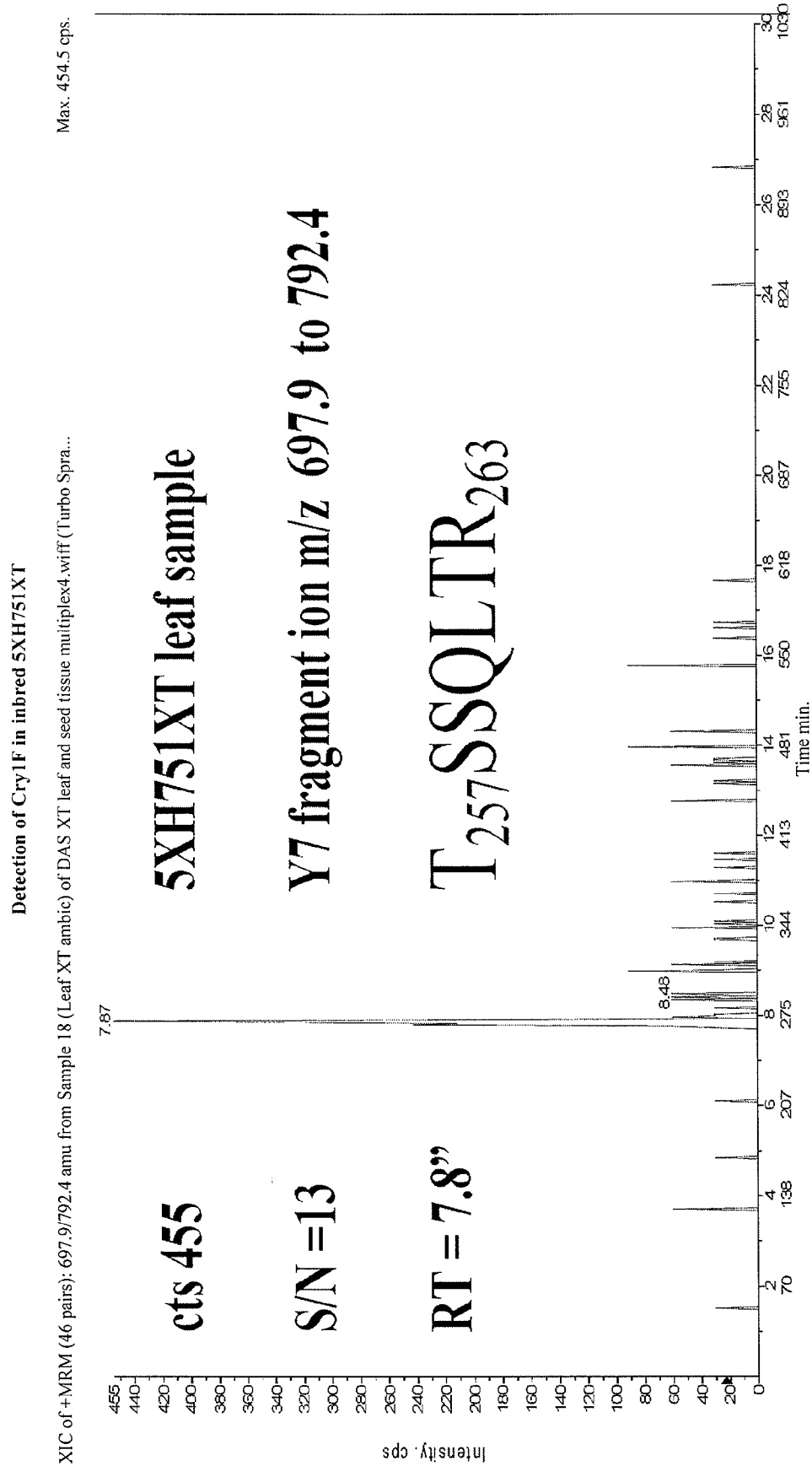
FIG. 7a includes detection of Y7 fragment ion TSSQLTR (SEQ ID NO:31).
Figure 7B:
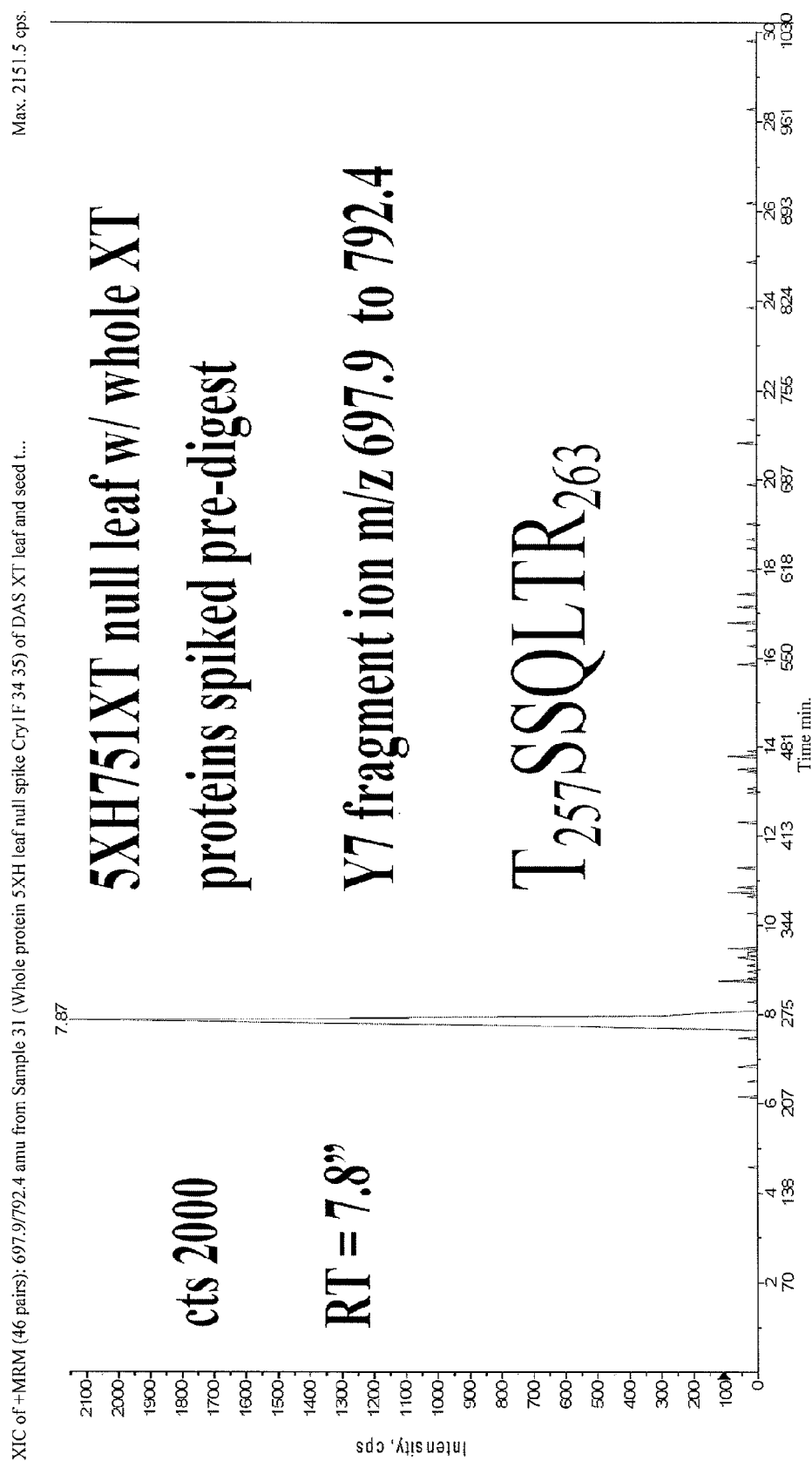
FIG. 7b includes detection of Y7 fragment ion TSSQLTR (SEQ ID NO:31).
Figure 7C:
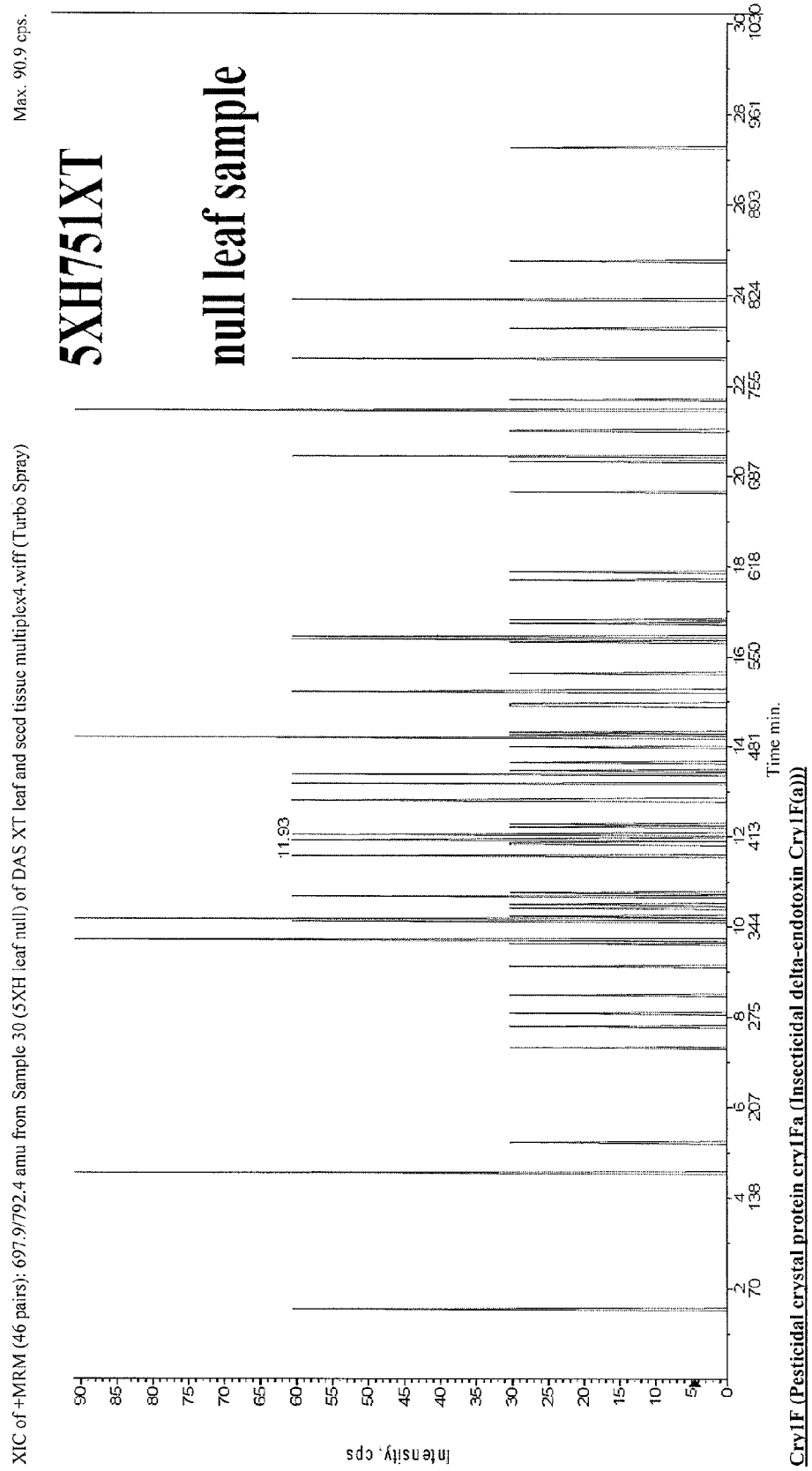
FIG. 7c includes a null leaf sample.

Specifically, FIG. 7 shows LC-MS/MS multiplex detection of Cry1F, expressed in inbred maize tissue. The data is a MS/MS spectra specific for Cry1F multiplex identified in 5XH751 maize leaf tissue extracted with 25 mM ammonium bicarbonate. Three Cry1F T22 specific fragment ions were detected, only one fragment shown here. Also shown are positive and negative controls for the MS/MS transition.

Figure 8A:
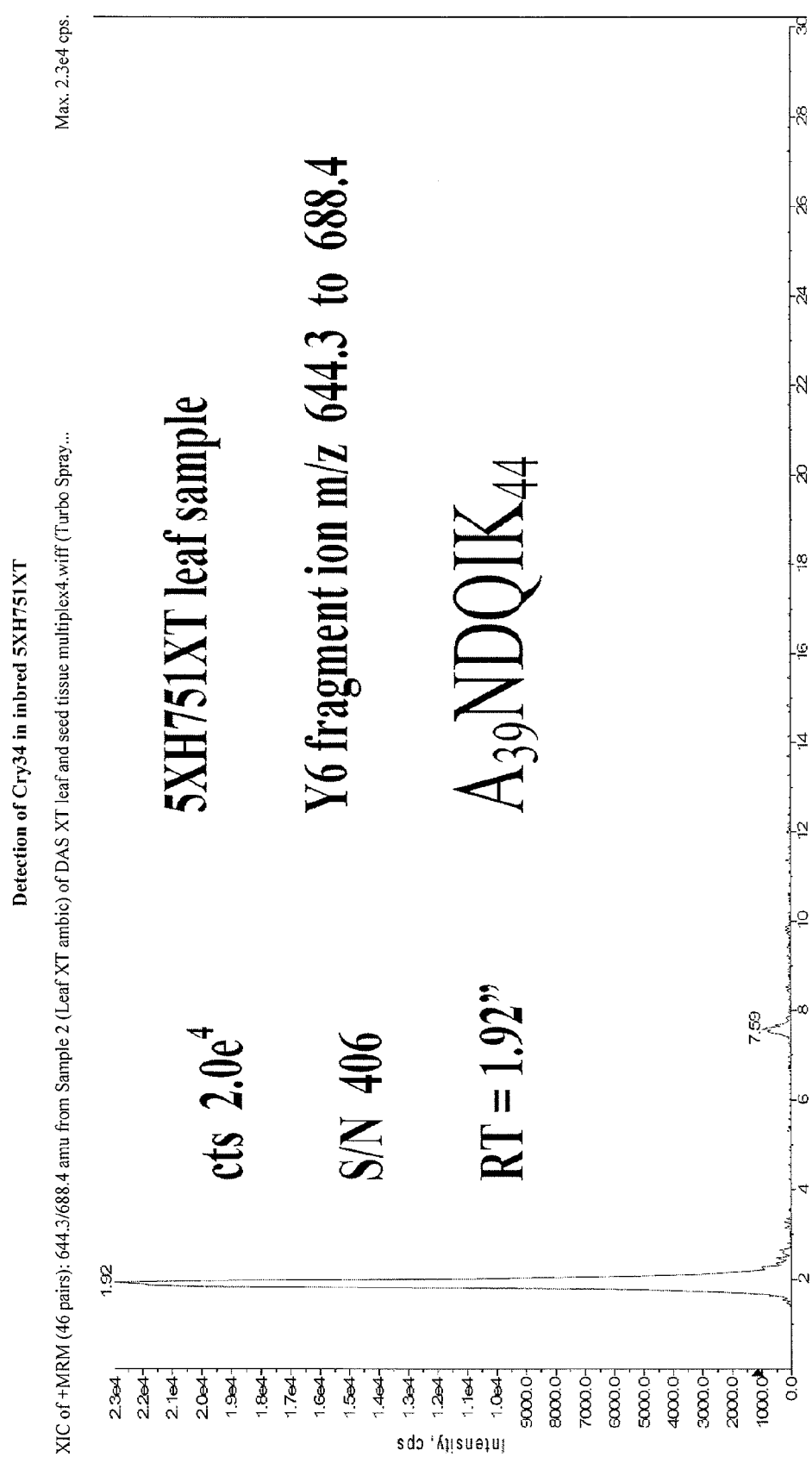
FIG. 8a includes detection of Y6 fragment ion ANDQIK (SEQ ID NO:25).
Figure 8B:
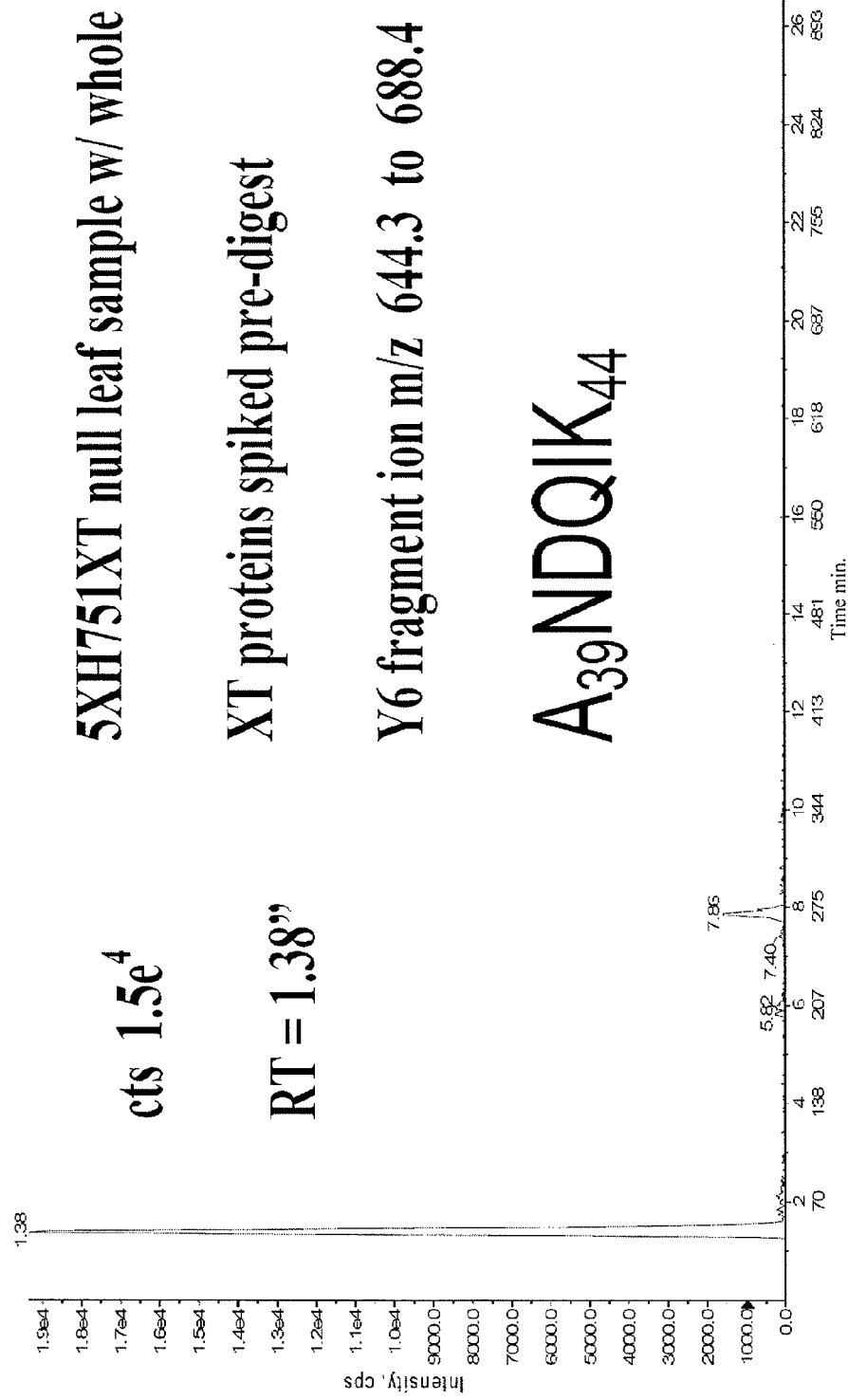
FIG. 8b includes detection of Y6 fragment ion ANDQIK (SEQ ID NO:25).
Figure 8C:
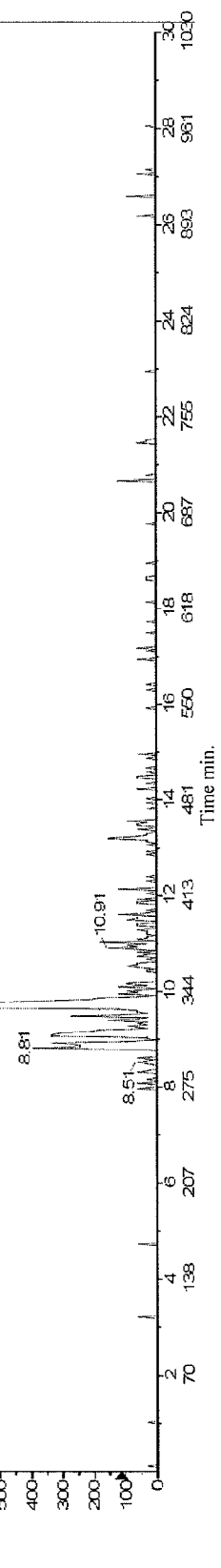
FIG. 8c includes a null leaf sample.

FIG. 8 shows LC-MS/MS multiplex detection of Cry34, expressed in inbred maize tissue. The data is a MS/MS spectra specific for Cry34, multiplex identified in 5XH751 maize leaf tissue extracted with 25 mM ammonium bicarbonate. Also shown are positive and negative controls for the MS/MS transition. Five Cry34 T7-specific fragment ions were detected, only one shown here. The slight shift in retention time between the 5XH751XT sample and the Cry34-fortified positive control is not unexpected for a protein eluting in the early, more hydrophilic region of the reverse phase gradient. The peak shown in the null leaf control panel is a non-specific peak as determined by the large (~7 min) shift in retention time from the column None of the other four Cry34 fragment ions had non-specific peaks.

Figure 9A:
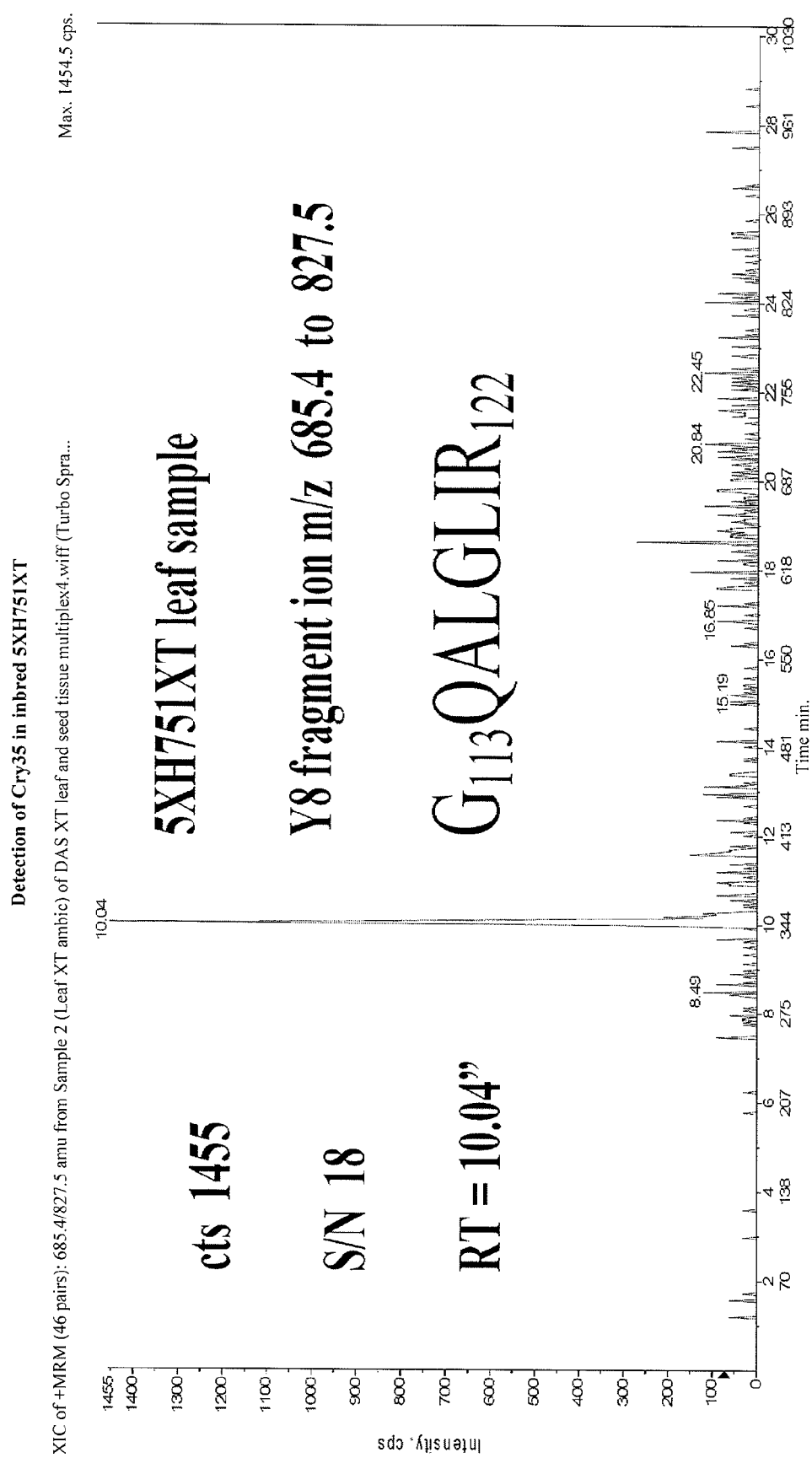
FIG. 9a includes detection of Y8 fragment ion GQALGLIR (SEQ ID NO:26).
Figure 9B:
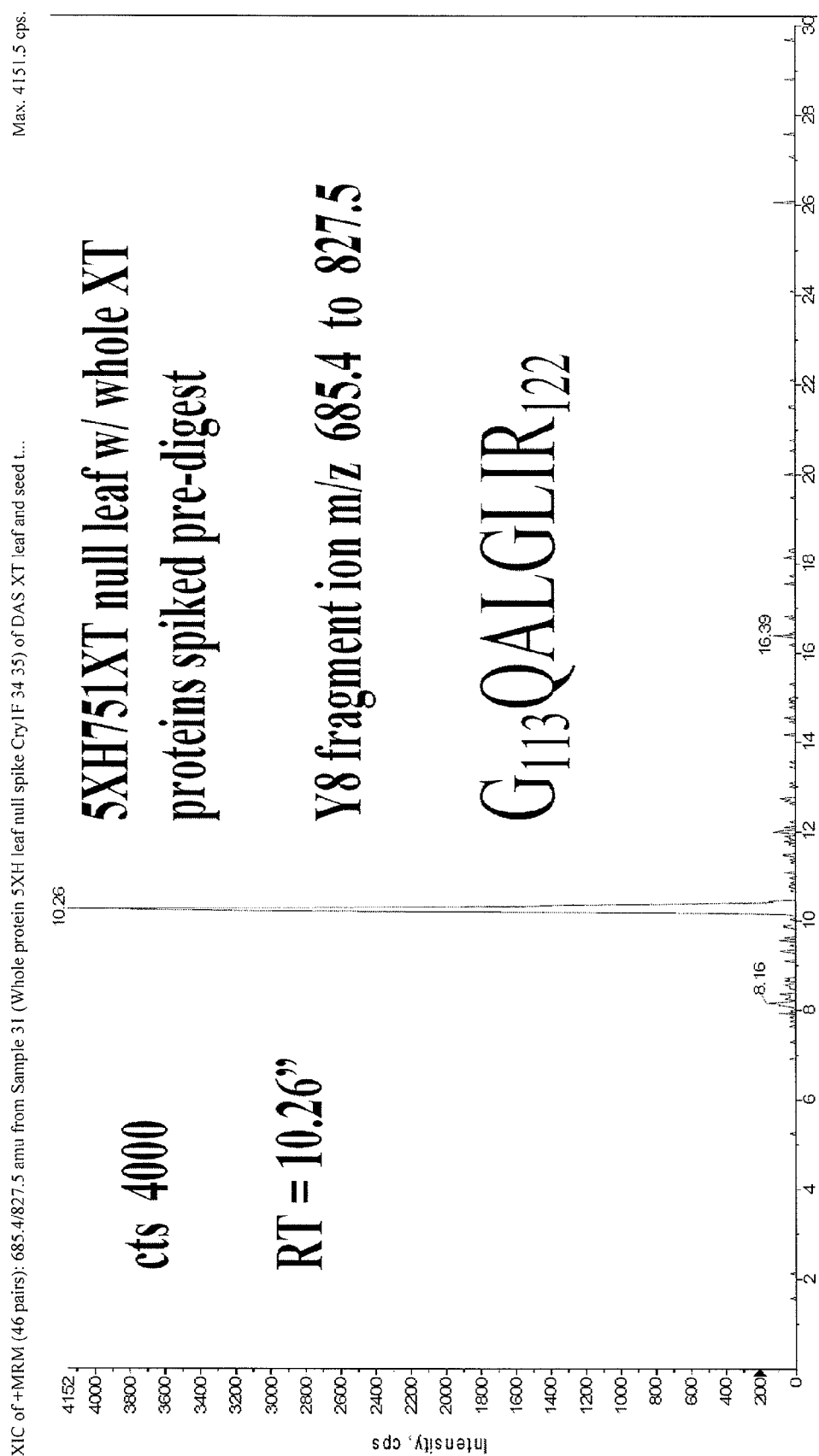
FIG. 9b includes detection of Y8 fragment ion GQALGLIR (SEQ ID NO:26).
Figure 9C:
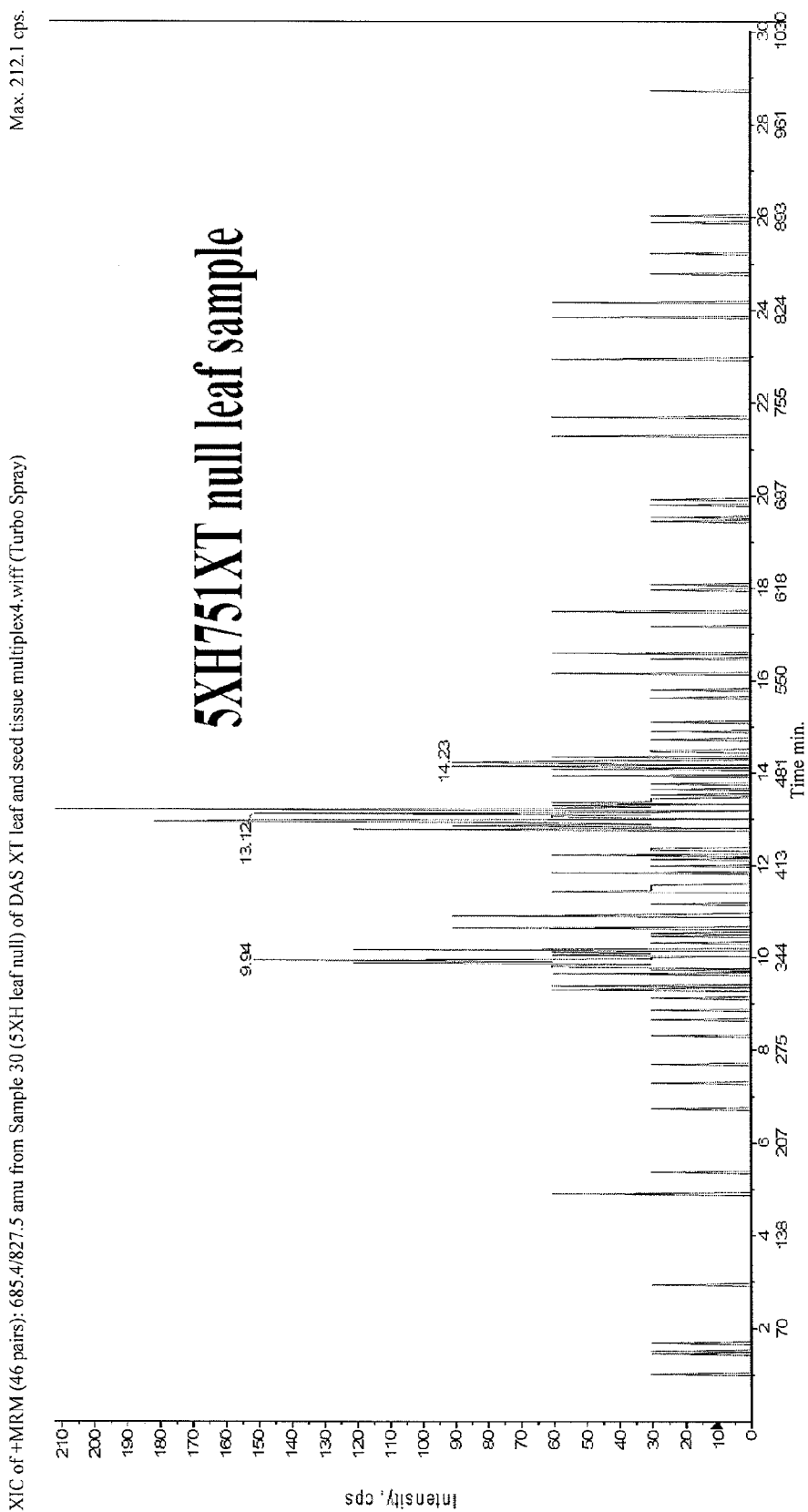
FIG. 9c includes a null leaf sample.

FIG. 9 shows LC-MS/MS multiplex detection of Cry35, expressed in inbred maize tissue. The data is a MS/MS spectra specific for Cry35, multiplex identified in maize leaf tissue. Also shown are positive and negative controls for the MS/MS transition. Data shown is from 5XH751 leaf tissue extracted with 25 mM ammonium bicarbonate. Three Cry35 T9-specific fragment ions were detected, only one shown here.

Figure 10A:
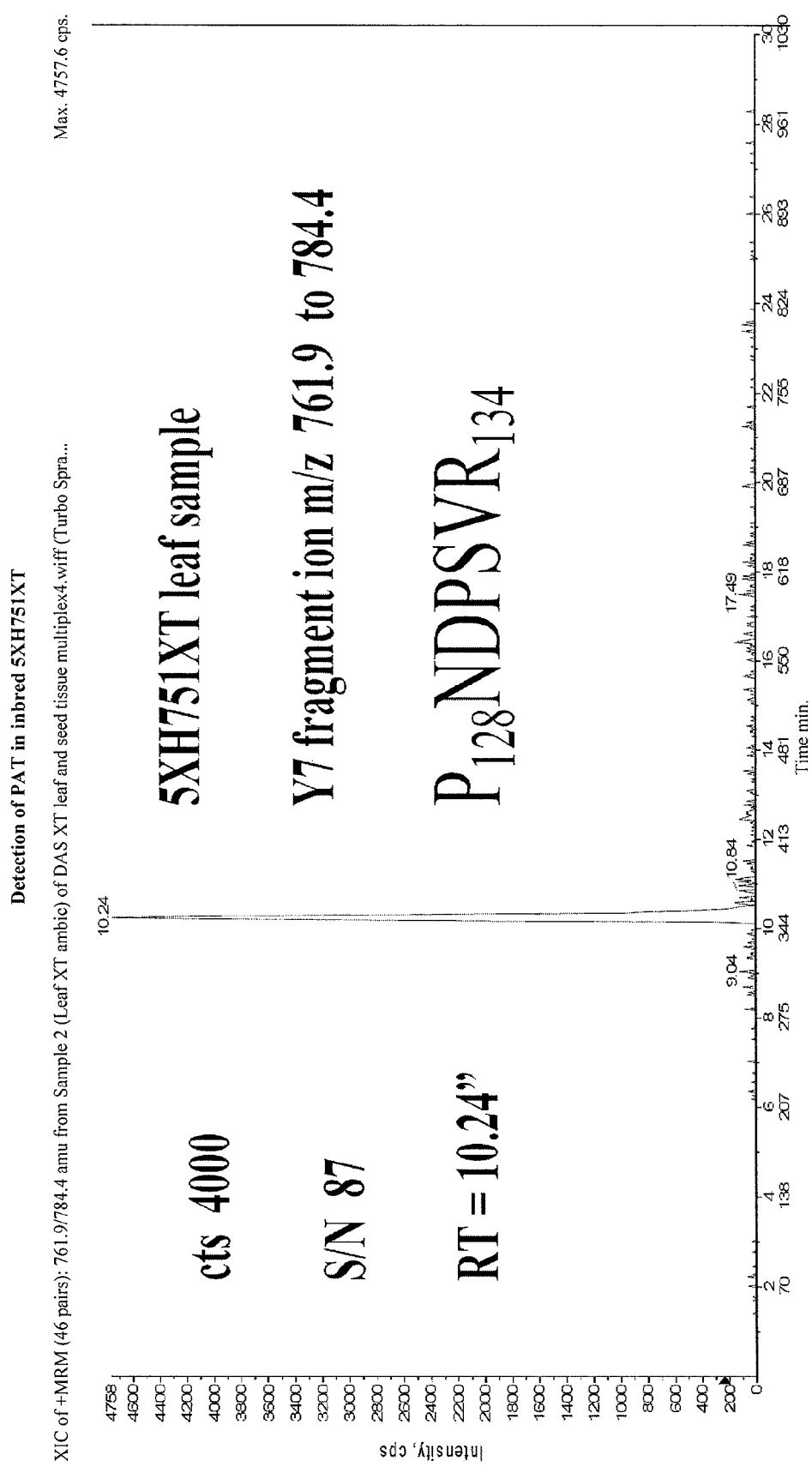
FIG. 10a includes detection of Y7 fragment ion PNDPSVR (SEQ ID NO:32).
Figure 10B:
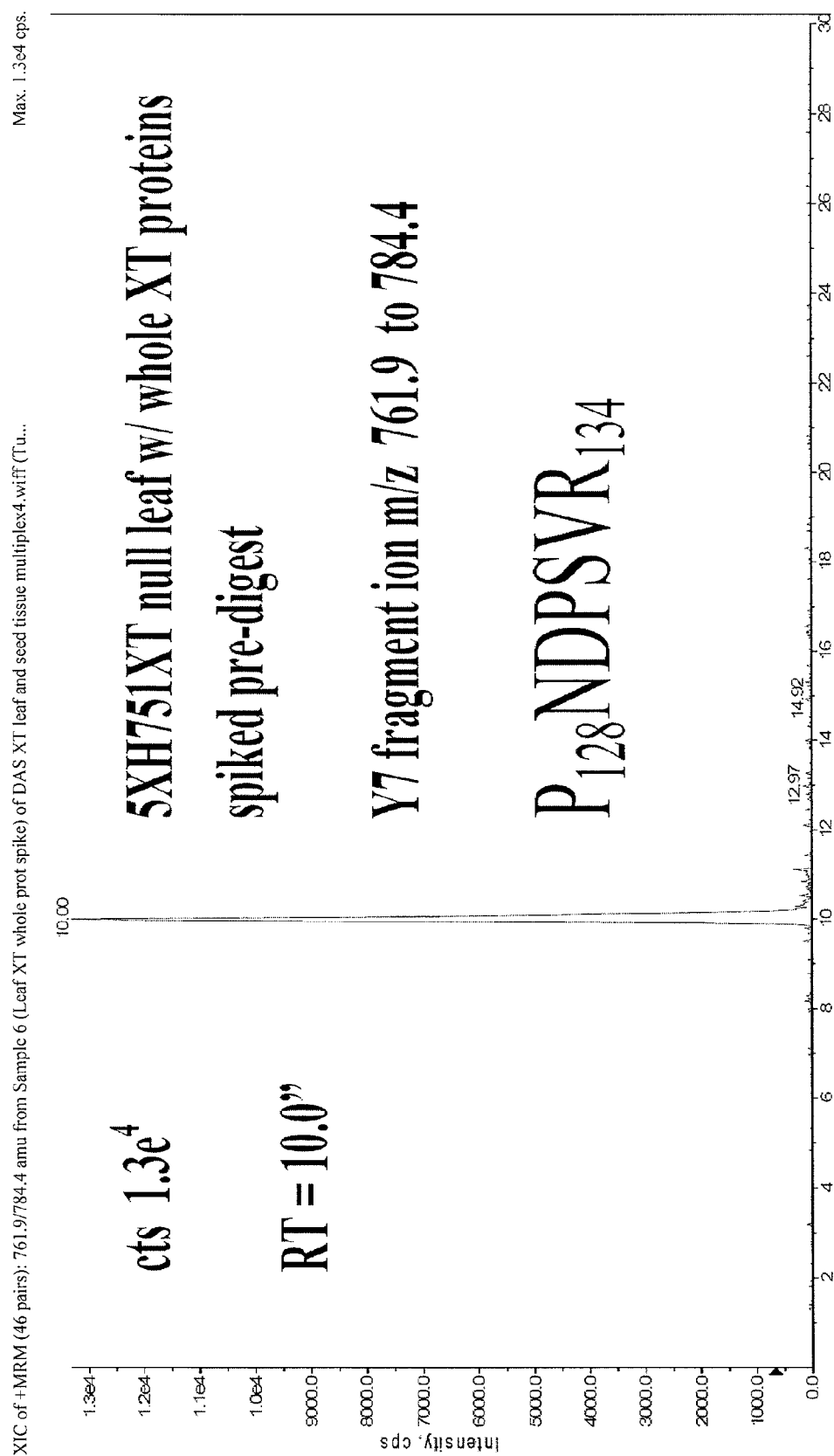
FIG. 10b includes detection of Y7 fragment ion PNDPSVR (SEQ ID NO:32).
Figure 10C:
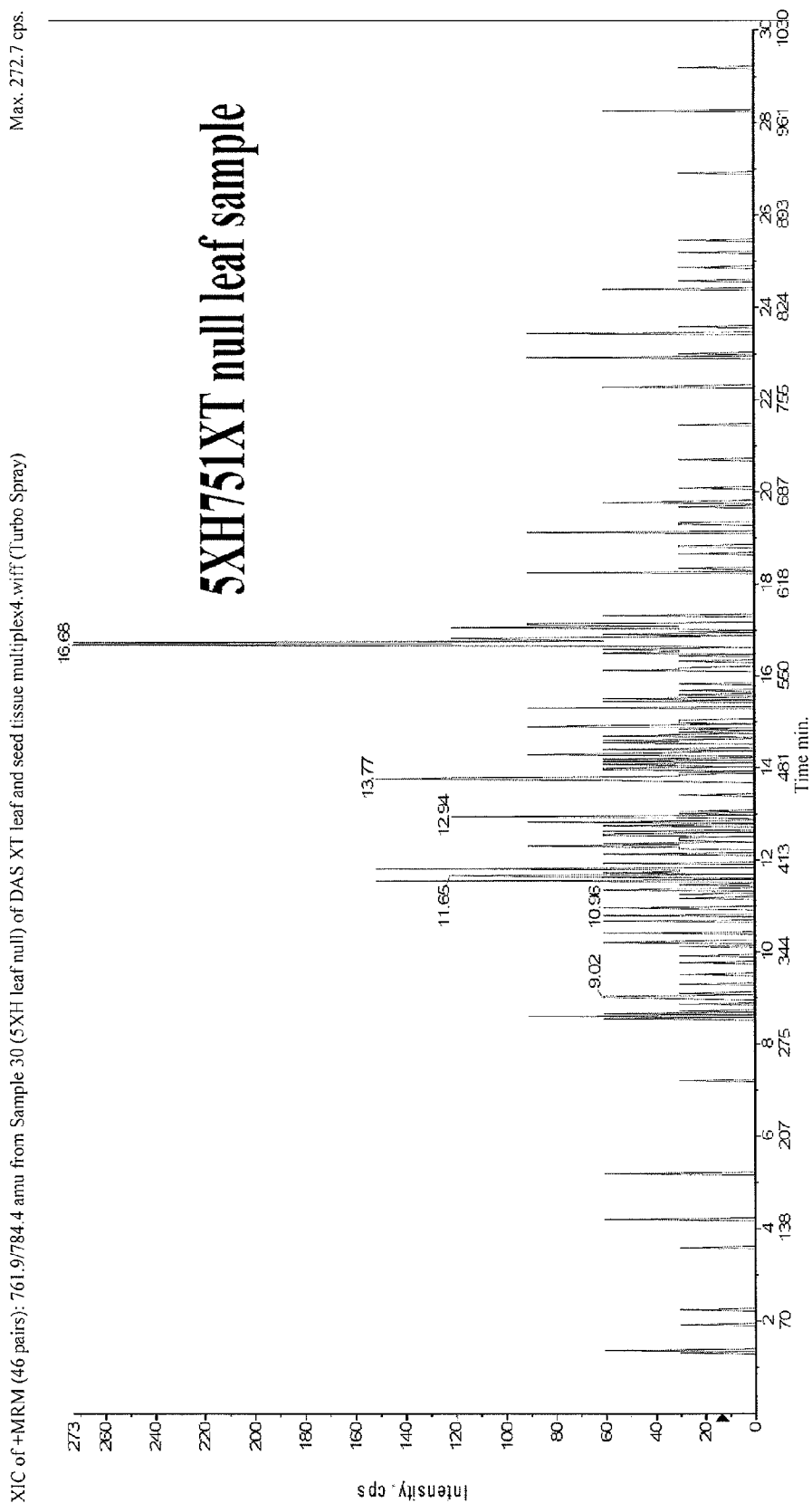
FIG. 10c includes a null leaf sample.

FIG. 10 shows LC/MS/MS multiplex detection of PAT, expressed in inbred maize tissue. The data is a MS/MS spectra specific for PAT, multiplex identified in maize leaf tissue. Also shown are positive and negative controls for the MS/MS transition.

For each protein, a specific precursor peptide was detected and fragmented, with three to five corresponding fragment ions detected to ensure protein sequence confirmation. FIGS. 7, 8, 9 and 10 each demonstrate a MS/MS spectra specific for one of the four proteins multiplex identified in maize tissue. Each figure also demonstrates the proper positive and negative control for the particular MS/MS transition. Two of the four proteins were detected in the seed tissue. The inability to detect two of the four proteins was likely due to low expression, as historical data demonstrate lower expression of these four proteins in seed as compared to leaf tissue.

Example V

A transgenic plant variety is maintained by confirming the presence of two proteins of interest in a next generation of the plant variety. A transgenic plant is selected wherein the transgenic plant comprises two transgenic proteins of interest (A and B). Samples of proteins A and B are prepared, and subjected to LC/MS/MS analysis. From the resulting MS spectra, fragment peptide ions of the parent proteins are selected for targeted MS/MS analysis.

A complex protein sample is prepared from a first generation of the transgenic plant, and the complex protein sample is subjected to a multiplex LC/MS/MS analysis, wherein the selected fragment peptide ions of proteins A and B are identified by determining the presence of the selected fragment peptide ions in the MS spectra. Complex protein samples are then prepared from plants of a next generation of the transgenic plant. The complex protein samples of these next-generation plants are subjected to a multiplex LC/MS/MS analysis. Those next-generation plants, from which the prepared complex protein samples produced MS spectra wherein the presence of both proteins A and B were identified from the presence of the selected fragment peptide ions, are propagated to maintain the transgenic plant variety. Those next-generation plants, from which the prepared complex protein samples produced MS spectra wherein the presence of both proteins A and B were not identified, are not propagated to maintain the transgenic plant variety.

Example VI

Transformants resulting from a plant transformation procedure are screened to determine the presence of two target proteins of interest. Two target proteins (A and B) are subjected to LC/MS/MS analysis. From the resulting MS spectra, fragment peptide ions of the parent target proteins are selected for targeted MS/MS analysis.

Putative transformants are obtained from a plant transformation procedure. Complex protein samples are prepared from each of the putative transformants. The complex protein samples of these putative transformants are subjected to a multiplex LC/MS/MS analysis, wherein the expression of the target proteins is determined by ascertaining the presence of the selected fragment peptide ions. Those transformants, from which the prepared complex protein samples produced MS spectra wherein desirable expression characteristics of proteins A and B were determined from the presence of the selected fragment peptide ions, are propagated.

Example VII

Bioconfinement of transgenes in a transgenic plant is achieved. Two target proteins (A and B) expressed by a transgenic plant are subjected to LC/MS/MS analysis. From the resulting MS spectra, fragment peptide ions of the parent target proteins are selected for targeted MS/MS analysis.

Plant material from plants growing in the environment surrounding the transgenic plant is collected. Complex protein samples are prepared from this plant material. The complex protein samples from these plant materials are subjected to a multiplex LC/MS/MS analysis, wherein the presence of a contaminating transgene is determined by ascertaining the presence of the selected fragment peptide ions of the expressed transgenic protein. Plants from which material was collected that were shown by the multiplex LC/MS/MS analysis to contain the contaminating transgenic protein are destroyed.

The following references are all hereby incorporated this reference it their entirety:
Alwine et al. (1977) *Proc. Nat. Acad. Sci.* 74:5350-54; Baldwin (2004) *Mol. Cell. Proteomics* 3(1):1-9; Can and Annan (1997) Overview of peptide and protein analysis by mass spectrometry. In: *Current Protocols in Molecular Biology*, edited by Ausubel, et al. New York: Wiley, p. 10.21.1-10.21.27; Chang et al. (2000) *Plant Physiol.* 122(2):295-317; Domon and Aebersold (2006) *Science* 312(5771): 212-17; Nain et al. (2005) *Plant Mol. Biol. Rep.* 23:59-65; Patterson (1998) Protein identification and characterization by mass spectrometry. In: *Current Protocols in Molecular Biology*, edited by Ausubel, et al. New York: Wiley, p. 10.22.1-10.22.24; Paterson and Aebersold (1995) *Electrophoresis* 16: 1791-1814; Rajagopal and Ahern (2001) *Science* 294(5551):2571-73; Sesikeran and Vasanthi (2008) *Asia Pac. J. Clin. Nutr.* 17 Suppl. 1:241-44; and Toplak et al. (2004) *Plant Mol. Biol. Rep.* 22:237-50.

What is claimed is:

1. A high-throughput method of detecting the presence of two or more proteins of interest with known amino acid sequences in a plant-based sample, the method comprising:
   extracting proteins from a plant-based sample
   digesting all of the extracted proteins to obtain peptides;
   separating the peptides in a single step;
   ionizing the peptides; and
   obtaining simultaneous mass spectral data for the peptides and determining the presence or absence of the two or more proteins of interest.

2. The method according to claim 1, wherein the peptides are separated in a single step by column chromatography.

3. The method according to claim 2, wherein the column chromatography is a liquid column chromatography.

4. The method according to claim 1, wherein the plant-based sample proteins are digested in a single step before injection.

5. The method according to claim 1, wherein the peptides are ionized in a single step.

6. The method according to claim 1, wherein the mass spectral data for the peptides corresponding to the two or more proteins of interest are obtained in a single step.

7. The method according to claim 1, wherein the two or more proteins of interest is two proteins of interest.

8. The method according to claim 1, wherein the two or more proteins of interest is four proteins of interest.

9. The method according to claim 1, wherein the plant-based sample is from a transgenic plant.

10. The method according to claim 1, wherein the plant-based sample is from a transgenic plant, and the two or more proteins of interest are expected products of transgene expression in the transgenic plant.

11. A high-throughput method of detecting the presence of two or more proteins of interest with known amino acid sequences in a plant-based sample, the method comprising:
   providing mass spectral data for two or more proteins of interest;
   providing a first injection of a complex plant-based sample comprising unseparated proteins;
   digesting the unseparated proteins into peptides;
   separating the peptides in a single step;
   ionizing the peptides;
   obtaining simultaneous mass spectral data for the peptides; and
   comparing the simultaneous mass spectral data to the mass spectral data provided for the two or more proteins of interest, thereby determining the presence or absence of the two or more proteins of interest.

12. The method according to claim 11, wherein the unseparated proteins are digested in a single step.

13. The method according to claim 11, wherein the peptides are ionized in a single step.

14. The method according to claim 11, wherein the plant-based sample is from a transgenic plant.

15. A method of maintaining the genotype of a transgenic plant variety, the method comprising:
   (i) providing mass spectral data for one or more expected product(s) of transgene expression in the transgenic plant variety;
   (ii) providing a first injection of a complex sample comprising unseparated proteins from a first generation of the transgenic plant variety;
   (iii) digesting the unseparated proteins into peptides;
   (iv) separating the peptides in a single step;
   (v) ionizing the peptides;
   (vi) obtaining simultaneous mass spectral data for the peptides, and comparing the simultaneous mass spectral data to the mass spectral data provided for the expected products of transgene expression, thereby determining the presence or absence of the expected products of transgene expression in the first generation of the transgenic plant variety;
   (vii) providing a first injection of a complex sample comprising unseparated proteins from a second generation of the transgenic plant variety;
   (viii) repeating steps (iii)-(vi) with the unseparated proteins from the second generation of the transgenic plant variety; and
   (ix) failing to propagate the second generation of the transgenic plant variety if the presence of the expected product(s) of transgene expression cannot be confirmed in the mass spectral data for the peptides from the complex protein sample from the second generation of the transgenic plant variety, thereby maintaining the genotype of the transgenic plant variety.

16. The method according to claim 15, wherein the proteins digested in step (iii) are digested in a single step.

17. The method according to claim 15, wherein the peptides ionized in step (v) are ionized in a single step.

* * * * *

SEQUENCE LISTING

```
<160> NUMBER OF SEQ ID NOS: 32

<210> SEQ ID NO 1
<211> LENGTH: 11
<212> TYPE: PRT
<213> ORGANISM: Artificial
<220> FEATURE:
<223> OTHER INFORMATION: Peptide T6 from AAD-1

<400> SEQUENCE: 1

Phe Gly Pro Val Asp Pro Val Pro Leu Leu Lys
1               5                   10
```

-continued

```
<210> SEQ ID NO 2
<211> LENGTH: 12
<212> TYPE: PRT
<213> ORGANISM: Artificial
<220> FEATURE:
<223> OTHER INFORMATION: Peptide T7 from AAD-1

<400> SEQUENCE: 2

Ser Ile Glu Gly Tyr Pro Glu Val Gln Met Ile Arg
1               5                   10

<210> SEQ ID NO 3
<211> LENGTH: 11
<212> TYPE: PRT
<213> ORGANISM: Artificial
<220> FEATURE:
<223> OTHER INFORMATION: Peptide T12 from AAD-1

<400> SEQUENCE: 3

Val Phe Gly Ser Leu Tyr Gln Ala Gln Asn Arg
1               5                   10

<210> SEQ ID NO 4
<211> LENGTH: 13
<212> TYPE: PRT
<213> ORGANISM: Artificial
<220> FEATURE:
<223> OTHER INFORMATION: Peptide T4 from AAD-12

<400> SEQUENCE: 4

Ile Gly Gly Gly Asp Ile Val Ala Ile Ser Asn Val Lys
1               5                   10

<210> SEQ ID NO 5
<211> LENGTH: 11
<212> TYPE: PRT
<213> ORGANISM: Artificial
<220> FEATURE:
<223> OTHER INFORMATION: Peptide T9 from AAD-12

<400> SEQUENCE: 5

Ala Ala Tyr Asp Ala Leu Asp Glu Ala Thr Arg
1               5                   10

<210> SEQ ID NO 6
<211> LENGTH: 7
<212> TYPE: PRT
<213> ORGANISM: Artificial
<220> FEATURE:
<223> OTHER INFORMATION: Peptide T19 from AAD-12

<400> SEQUENCE: 6

Ala Glu Pro Trp Asp Phe Lys
1               5

<210> SEQ ID NO 7
<211> LENGTH: 12
<212> TYPE: PRT
<213> ORGANISM: Artificial
<220> FEATURE:
<223> OTHER INFORMATION: Peptide T22 from Cry1F

<400> SEQUENCE: 7

Thr Tyr Pro Ile Gln Thr Ser Ser Gln Leu Thr Arg
1               5                   10

<210> SEQ ID NO 8
```

```
<211> LENGTH: 8
<212> TYPE: PRT
<213> ORGANISM: Artificial
<220> FEATURE:
<223> OTHER INFORMATION: Peptide T46 from Cry1F

<400> SEQUENCE: 8

Ile Phe Ala Gly Gln Phe Asn Lys
1               5

<210> SEQ ID NO 9
<211> LENGTH: 12
<212> TYPE: PRT
<213> ORGANISM: Artificial
<220> FEATURE:
<223> OTHER INFORMATION: Peptide T7 from Cry34

<400> SEQUENCE: 9

Thr Ser Pro Thr Asn Val Ala Asn Asp Gln Ile Lys
1               5                   10

<210> SEQ ID NO 10
<211> LENGTH: 14
<212> TYPE: PRT
<213> ORGANISM: Artificial
<220> FEATURE:
<223> OTHER INFORMATION: Peptide T9 from Cry35

<400> SEQUENCE: 10

Val Leu Thr Ala Gly Thr Gly Gln Ala Leu Gly Leu Ile Arg
1               5                   10

<210> SEQ ID NO 11
<211> LENGTH: 6
<212> TYPE: PRT
<213> ORGANISM: Artificial
<220> FEATURE:
<223> OTHER INFORMATION: Peptide T17 from Cry35

<400> SEQUENCE: 11

Tyr Gln Tyr Trp Gln Arg
1               5

<210> SEQ ID NO 12
<211> LENGTH: 15
<212> TYPE: PRT
<213> ORGANISM: Artificial
<220> FEATURE:
<223> OTHER INFORMATION: Peptide T2 from PAT

<400> SEQUENCE: 12

Thr Glu Pro Gln Thr Pro Gln Glu Trp Ile Asp Asp Leu Glu Arg
1               5                   10                  15

<210> SEQ ID NO 13
<211> LENGTH: 13
<212> TYPE: PRT
<213> ORGANISM: Artificial
<220> FEATURE:
<223> OTHER INFORMATION: Peptide T8 from PAT

<400> SEQUENCE: 13

Leu Gly Leu Gly Ser Thr Leu Tyr Thr His Leu Leu Lys
1               5                   10

<210> SEQ ID NO 14
<211> LENGTH: 15
<212> TYPE: PRT
```

-continued

```
<213> ORGANISM: Artificial
<220> FEATURE:
<223> OTHER INFORMATION: Peptide T10 from PAT

<400> SEQUENCE: 14

Ser Val Val Ala Val Ile Gly Leu Pro Asn Asp Pro Ser Val Arg
1               5                   10                  15

<210> SEQ ID NO 15
<211> LENGTH: 7
<212> TYPE: PRT
<213> ORGANISM: Artificial
<220> FEATURE:
<223> OTHER INFORMATION: Y7 fragment ion from peptide T6 of AAD-1

<400> SEQUENCE: 15

Pro Glu Val Gln Met Ile Arg
1               5

<210> SEQ ID NO 16
<211> LENGTH: 6
<212> TYPE: PRT
<213> ORGANISM: Artificial
<220> FEATURE:
<223> OTHER INFORMATION: Y6 fragment from peptide T6 from AAD-1

<400> SEQUENCE: 16

Pro Val Pro Leu Leu Lys
1               5

<210> SEQ ID NO 17
<211> LENGTH: 6
<212> TYPE: PRT
<213> ORGANISM: Artificial
<220> FEATURE:
<223> OTHER INFORMATION: Y6 fragment from peptide T12 from AAD-1

<400> SEQUENCE: 17

Tyr Gln Ala Gln Asn Arg
1               5

<210> SEQ ID NO 18
<211> LENGTH: 8
<212> TYPE: PRT
<213> ORGANISM: Artificial
<220> FEATURE:
<223> OTHER INFORMATION: Y8 fragment from peptide T9 from AAD-12

<400> SEQUENCE: 18

Asp Ala Leu Asp Glu Ala Thr Arg
1               5

<210> SEQ ID NO 19
<211> LENGTH: 5
<212> TYPE: PRT
<213> ORGANISM: Artificial
<220> FEATURE:
<223> OTHER INFORMATION: Y5 fragment from peptide T19 from AAD-12

<400> SEQUENCE: 19

Asp Pro Ser Val Arg
1               5

<210> SEQ ID NO 20
<211> LENGTH: 7
<212> TYPE: PRT
<213> ORGANISM: Artificial
<220> FEATURE:
```

```
<223> OTHER INFORMATION: Y7 fragment from peptide T4 from AAD-12

<400> SEQUENCE: 20

Val Ala Ile Ser Asn Val Lys
1               5

<210> SEQ ID NO 21
<211> LENGTH: 8
<212> TYPE: PRT
<213> ORGANISM: Artificial
<220> FEATURE:
<223> OTHER INFORMATION: Y8 fragment from peptide T22 from Cry1F

<400> SEQUENCE: 21

Gln Thr Ser Ser Gln Leu Thr Arg
1               5

<210> SEQ ID NO 22
<211> LENGTH: 10
<212> TYPE: PRT
<213> ORGANISM: Artificial
<220> FEATURE:
<223> OTHER INFORMATION: Y10 fragment from peptide T22 from Cry1F

<400> SEQUENCE: 22

Pro Ile Gln Thr Ser Ser Gln Leu Thr Arg
1               5                   10

<210> SEQ ID NO 23
<211> LENGTH: 6
<212> TYPE: PRT
<213> ORGANISM: Artificial
<220> FEATURE:
<223> OTHER INFORMATION: Y6 fragment from peptide T46 from Cry1F

<400> SEQUENCE: 23

Ala Gly Gln Phe Asn Lys
1               5

<210> SEQ ID NO 24
<211> LENGTH: 5
<212> TYPE: PRT
<213> ORGANISM: Artificial
<220> FEATURE:
<223> OTHER INFORMATION: Y5 fragment from peptide t7 from Cry34

<400> SEQUENCE: 24

Asn Asp Gln Ile Lys
1               5

<210> SEQ ID NO 25
<211> LENGTH: 6
<212> TYPE: PRT
<213> ORGANISM: Artificial
<220> FEATURE:
<223> OTHER INFORMATION: Y6 fragment from peptide T7 from Cry34

<400> SEQUENCE: 25

Ala Asn Asp Gln Ile Lys
1               5

<210> SEQ ID NO 26
<211> LENGTH: 8
<212> TYPE: PRT
<213> ORGANISM: Artificial
<220> FEATURE:
<223> OTHER INFORMATION: Y8 fragment from peptide T9 from Cry35
```

```
<400> SEQUENCE: 26

Gly Gln Ala Leu Gly Leu Ile Arg
1               5

<210> SEQ ID NO 27
<211> LENGTH: 10
<212> TYPE: PRT
<213> ORGANISM: Artificial
<220> FEATURE:
<223> OTHER INFORMATION: Y10 fragment from peptide T9 from Cry35

<400> SEQUENCE: 27

Gly Thr Gly Gln Ala Leu Gly Leu Ile Arg
1               5                   10

<210> SEQ ID NO 28
<211> LENGTH: 9
<212> TYPE: PRT
<213> ORGANISM: Artificial
<220> FEATURE:
<223> OTHER INFORMATION: Y9 fragment from peptide T10 from PAT

<400> SEQUENCE: 28

Gly Leu Pro Asn Asp Pro Ser Val Arg
1               5

<210> SEQ ID NO 29
<211> LENGTH: 10
<212> TYPE: PRT
<213> ORGANISM: Artificial
<220> FEATURE:
<223> OTHER INFORMATION: Y10 fragment from peptide T2 from PAT

<400> SEQUENCE: 29

Pro Gln Glu Trp Ile Asp Asp Leu Glu Arg
1               5                   10

<210> SEQ ID NO 30
<211> LENGTH: 10
<212> TYPE: PRT
<213> ORGANISM: Artificial
<220> FEATURE:
<223> OTHER INFORMATION: Y10 fragment from peptide T8 from PAT

<400> SEQUENCE: 30

Gly Ser Thr Leu Tyr Thr His Leu Leu Lys
1               5                   10

<210> SEQ ID NO 31
<211> LENGTH: 7
<212> TYPE: PRT
<213> ORGANISM: Artificial
<220> FEATURE:
<223> OTHER INFORMATION: Y7 fragment from Cry1F

<400> SEQUENCE: 31

Thr Ser Ser Gln Leu Thr Arg
1               5

<210> SEQ ID NO 32
<211> LENGTH: 7
<212> TYPE: PRT
<213> ORGANISM: Artificial
```

```
<220> FEATURE:
<223> OTHER INFORMATION: Y7 fragment from PAT

<400> SEQUENCE: 32

Pro Asn Asp Pro Ser Val Arg
1               5
```